United States Patent
Behar-Cohen et al.

(10) Patent No.: US 8,039,445 B2
(45) Date of Patent: Oct. 18, 2011

(54) METHODS AND DEVICES FOR DELIVERING A THERAPEUTIC PRODUCT TO THE OCULAR SPHERE OF A SUBJECT

(75) Inventors: Francine Behar-Cohen, Paris (FR); David Benezra, Jerusalem (IL); Pascal Bigey, Paris (FR); Carole Bloquel, Paris (FR); Daniel Scherman, Paris (FR)

(73) Assignee: INSERM (Institut National de la Sante et de la Recherche Medicale), Paris (FR)

( * ) Notice: Subject to any disclaimer, the term of this patent is extended or adjusted under 35 U.S.C. 154(b) by 673 days.

(21) Appl. No.: 11/911,771

(22) PCT Filed: Apr. 18, 2006

(86) PCT No.: PCT/IB2006/001667
§ 371 (c)(1),
(2), (4) Date: Oct. 17, 2007

(87) PCT Pub. No.: WO2006/123248
PCT Pub. Date: Nov. 23, 2006

(65) Prior Publication Data
US 2008/0183123 A1    Jul. 31, 2008

(30) Foreign Application Priority Data
Apr. 18, 2005 (EP) ..................... 05290855

(51) Int. Cl.
*A61K 48/00* (2006.01)
*C12N 15/00* (2006.01)
*C12N 15/87* (2006.01)

(52) U.S. Cl. ....................... 514/44 R; 435/455; 435/461

(58) Field of Classification Search ............... None
See application file for complete search history.

(56) References Cited

U.S. PATENT DOCUMENTS
5,944,710 A * 8/1999 Dev et al. ..................... 604/500
6,204,251 B1 3/2001 Cuthbertson

FOREIGN PATENT DOCUMENTS
EP    0 927 560    7/1999
EP    1 452 203    9/2004

OTHER PUBLICATIONS

Borrás et al. IOVS 2002;8:2513-8.*
Borrás, Exp Eye Res 2003;76:643-52.*
Mamiya et al. Exp Eye Res 2004;79:405-10.*
Voigt et al. Biochem Biophy Res Comm 2002;295:336-41.*
McLoon et al. IOVS 2003;44:3866-72.*
Lemaitre et al. IOVS 2001;42:2022-30.*
Scott, "Botulinum Toxin Injection into Extra Ocular Muscles as an Alternative to Strabismus Surgery", XP002396760, Database Accession No. PREV198171054950, Abstract, Ophthalmology, 1980; 87: 1044-9.
Bloquel, et al., "Plasmid Electrotransfer of Eye Ciliary Muscle: Principles and Therapeutic Efficacy Using hTNF-α Soluble Receptor in Uveitis", The FASEB Journal, express article 10,1096/fj.05-4737fje, Dec. 13, 2005.
Dezawa, et al., "Gene transfer into retinal ganglion cells by in vivo electroporation: a new approach", Micron, vol. 33, p. 1-6, 2002.
Matsuda and Cepko, "Electroporation and RNA interference in the rodent retina in vivo and in vitro", PNAS, vol. 101, No. 1, p. 16-22, Jan. 6, 2004.
Spencer, et al., "Herpes Simplex Virus-Mediated Gene Delivery to the Rodent Visual System", Investigative Ophthalmology & Visual Science, vol. 41, No. 6, May 2000.

* cited by examiner

*Primary Examiner* — Q. Janice Li
(74) *Attorney, Agent, or Firm* — Hunton & Williams LLP

(57) ABSTRACT

The present invention relates, generally, to improved methods of delivering a biologically active agent, in particular a therapeutic or prophylactic nucleic acid, to the ocular sphere of a subject comprising administering said agent to the ciliary body tissue(s) or cells and/or to the extra-ocular muscle tissue or cells. More particularly, the invention relates to devices, their uses, notably in gene therapy, and to methods for treating pathologies of the ocular sphere by specific ciliary body tissue(s) or cells and/or extra-ocular muscle or cells administration of a therapeutic product and transfer thereof into the ocular tissue to be treated. This invention also relates to pharmaceutical compositions comprising the product in a form suitable for ciliary body tissue(s) or cells and/or extra-ocular muscle or cells administration, their preparation and uses.

22 Claims, 17 Drawing Sheets

Figure 1A:
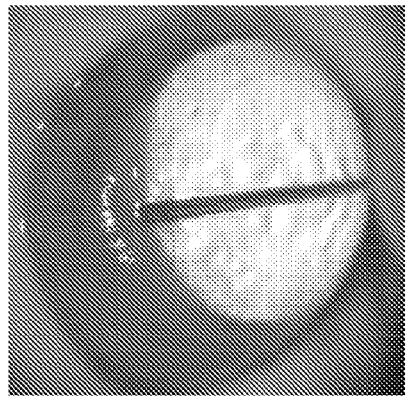

METHODS AND DEVICES FOR DELIVERING A THERAPEUTIC PRODUCT TO THE OCULAR SPHERE OF A SUBJECT

CROSS-REFERENCE TO RELATED APPLICATIONS

This application is the U.S. National Stage filing of International Application No. PCT/IB2006/001667, filed Apr. 18, 2006, which claims priority to EP 05290855.5, filed Apr. 18, 2005, the disclosure of which is hereby incorporated by reference.

The present invention relates, generally, to improved methods of delivering a biologically active agent, in particular a therapeutic or prophylactic nucleic acid, to the ocular sphere of a subject comprising administering said agent to the ciliary body tissue(s) or cells and/or to the extra-ocular muscle tissue or cells. More particularly, the invention relates to devices, their uses, notably in gene therapy, and to methods for treating pathologies of the ocular sphere by specific ciliary body tissue(s) or cells and/or extra-ocular muscle tissue or cells administration of a therapeutic product, allowing the transfer thereof into the ocular tissue(s) to be treated. This invention also relates to pharmaceutical compositions comprising the product in a form suitable for ciliary body tissue(s) or cells and/or extra-ocular muscle tissue or cells administration, their preparation and uses.

BACKGROUND OF THE INVENTION

Anatomy of the Eye

The eye is one of the most complex organs in the body. Part of the eye is developmentally an extension of the central nervous system. The eye is composed of several parts and optimal vision or health and diseases of the eye depend on how the various parts work together.

The eye can anatomically and functionally be divided into a small anterior chamber and a large posterior chamber. Both chambers are separated by the lens which is a transparent and biconvex body. The lens is connected with fibres to the ciliary muscle which by contraction or relaxation alters its shape and focusing power. The ciliary muscle is a non skeletal muscle.

The posterior chamber is filled with the vitreous body, a transparent, and viscous fluid or gel-like structure composed of a network of collagen fibres suspended in a liquid containing hyaluronic acid.

The globe of the eye is built up by three layers. The outermost layer consists of two parts: the sclera and, at the front pole, the cornea. Beneath the sciera is the choroid. Finally, the innermost and light sensitive layer is termed the retina. The sclera is a protective sheet also known as the white part of the eye. It is a 0.3-1 mm thick layer of collagenous fibres which covers approximately 80% of the surface of the eyeball.

At the front of the eye, the transparent cornea bulges out of from the sclera as the dome-shaped "window of the eye". The human cornea is composed of 5 layers, i.e., the epithelium, the Bowman's membrane, the stroma, the Descemet's membrane and the endothelium. These layers are important for maintaining transparency of the cornea by a proper fluid balance and for preventing the entry of harmful agents into the eye. Only two of the 5 layers of the cornea, the epithelium and the stroma, are major barriers for drug passage into the eye. The endothelium like Bowman's and Descemet's membranes has no great influence on drug passage.

The corneal epithelium itself consists of five to six layers of cells with a total thickness of 50-100 µm that forms a lipophilic barrier for drugs. It has a protective function by preventing the entry of harmful agents into the eye and is also a fluid secreting tissue that assists the endothelium in maintaining stromal hydration and thereby corneal transparency. The cells of the epithelium are highly regenerative and have the ability to replace themselves within 3 days following injury. The stroma which represents 90% of the corneal thickness contains 75-80% water interspersed with collagen fibres and therefore represents a highly hydrophilic compartment.

Beneath the sclera, is the choroid which contains nerves and blood vessels which supply blood to the eye and drain it out. The choroid thickens at the front of the eye to form the ciliary body, which secretes a watery liquid called the aqueous humor.

Attached to the ciliary body is the iris, the colored part of the eye, which surrounds a central gap called the pupil. The primary function of the iris is to control the size of the pupil and therefore the amount of light entering the eye. This is achieved, as explained above, via contraction of the sphincter muscle and constriction of the dilator muscle. The pigmented melanin which gives the iris its color, aids in the absorption of strong or bright light.

The innermost layer of the eye containing the photosensitive cells is termed retina. Retina is composed of several layers, one being the photoreceptor layer which comprises cones, which are responsible for color vision, and rods for vision in dim light. Most of the cones are localized in a small-circumscribed area called the macula.

The aqueous humor has nutritive functions in particular for avascular structures of the eye such as the cornea, the lens and vitreous body. Aqueous humor is continually produced by the ciliary processes of the non-pigmented epithelium of the ciliary body at a rate of approximately 2.5 µL/min.

Extra-ocular muscles are responsible for the ocular mobility. They originate at the orbital apex and terminate on the globe. In their course, the extraocular muscles are also attached by the means of fibrous septa to the orbit. Anteriorly, the fascia planes blend with tenon's capsule, enclosing the sclera. In the human eye, the "extraocular muscle", in the sense of the invention, is constituted by four rectus muscles and two oblique muscles. The rectus muscles insert anteriorly at about 7 mm posterior to the limbus. The other extraocular muscles are the orbicular muscle that is responsible for the opening and closing of the eyelids and the Muller's fibres that have connections with the superior rectus muscle.

Problems for Delivering Drugs to the Eye

A major problem in the treatment of eye diseases and disorders is the difficulty in delivering biologically active agents into the eye at therapeutically or prophylactically effective concentrations. Oral administration of ocular drugs is mostly inadequate to target the retinal tissues due to the hemato-retinal barriers.

In order for an effective amount of a therapeutic agent to reach the ocular area, a high concentration of drug must frequently be administered. This can result in systemic toxicity. For example, pulse therapy may be used to reach high levels of corticosteroids in the eye.

There are also problems associated with the currently practiced methods of topical administration of ocular drugs. Topical administration is generally only effective in pathologies involving the superficial surface of the eye, i.e., the cornea and anterior segments. Currently practiced methods of topical drug administration are indeed ineffective in achieving adequate drug concentrations in some ocular tissues, particularly the intraocular tissues such as iris and ciliary body. It is even more difficult to reach the retina, optic nerve or vitreous body of the eye. In addition, topical administration is even less effective when the drug is a protein or peptide which typically lacks the ability to cross the cornea rendering the treatment of the intraocular diseases all the more difficult. Consequently, most current treatments for intraocular diseases are invasive as they frequently require intraocular needle injection or intraocular surgery (for example surgical implantation of slow release systems or encapsulated modified cells).

Extraocular inserts also have disadvantages. Frequent re-application is necessary because the therapeutic compound dissolves in a matter of hours. Again, these inserts only deliver drug to the cornea and anterior chamber.

Thus, despite the above-described attempts to provide effective treatment, there remains a long-felt and acute need for new approaches to treat ocular diseases, in particular intra-ocular diseases.

It would be of particular interest to define suitable methods for introducing therapeutic products, in particular proteins or nucleic acids, into the eye to control said diseases. Gene therapy, in particular, is emerging as an effective approach for management and treatment of a variety of diseases. Examples of effective gene therapy regimens appear routinely in the literature [see for example Roth et al., Nature Medicine, Vol. 2, 985-991 (1996), or Hermiston and Kim, Mol Therapy, vol 11, 496-508, (2005)]. Therapeutic gene transfer offers potential advantages such as continuous and/or targeted production of the desired transgene in vivo. Currently it is however difficult to perform nucleic acid transduction in ocular mammalian cells with great degree of effectiveness. It is in particular problematic to introduce these nucleic acids into the eye without induction of an inflammatory response. Further, there is a lack of means of transducing terminally differentiated or proliferating human cells within the eye. The present invention fulfills these long-standing needs and desires in the art.

The present inventors have indeed developed a method for delivering a pharmacologically active agent, in particular a therapeutic or prophylactic nucleic acid, to the ocular area, comprising administering said agent into the ciliary body tissue(s) or cells and/or into the extra-ocular muscle tissue or cells of a subject.

SUMMARY OF THE INVENTION

The present invention now provides compositions and methods for safe and efficient prevention or treatment of an ocular disease of an animal subject, preferably a mammalian subject, particularly a human subject. The present invention is based on the discovery that the ciliary body (comprising the ciliary muscle tissue and the ciliary epithelium), preferably the ciliary muscle, and/or the extra-ocular muscle may be used as a supply tank of pharmaceutical products for the ocular sphere, in particular for the inner and posterior parts of the eye.

The present invention describes a particularly efficient method for the selective transfer of a biologically or pharmacologically active agent, especially a nucleic acid, into the ocular sphere of a subject comprising administration of said agent into the ciliary body tissue(s) or cells and/or the extra-ocular muscle tissue or cells.

The invention further relates to the use of such a method to prevent or treat various ocular diseases, including but not limited to ocular inflammatory diseases, ischemic diseases, proliferative diseases, neurodegenerative diseases and glaucoma, either alone or in combination with additional treatments.

A second aspect of this invention is to the use of a therapeutic nucleic acid for preparing a composition for the treatment of an ocular disease by administering said composition to the ciliary body tissue(s) or cells and/or to the extra-ocular muscle tissue or cells of the subject to be treated.

The invention also relates to an electroporation device for administering an agent or a composition to the ciliary body tissue(s) or cells and/or to the extra-ocular muscle tissue or cells of a subject, comprising (i) at least one means for injecting the composition into said tissue(s) or cells, wherein said injection means is an injection needle, an injection needle electrode, a microneedle array comprising at least one injection needle or one injection needle electrode, or a combination thereof, (ii) optionally, a means for sensing when the needle has been inserted to a sufficient depth for injection of the composition to commence, said depth being preferably comprised between 0.1 and 10 mm, even more preferably between 0.1 and 0.9 mm, (iii) optionally, a means to position said injection means on the surface of the sclera or eye conjunctiva, and (iv) optionally, a means for generating a predetermined electric signal.

A further aspect of this invention is to the use, in gene therapy, of an electroporation device according to the invention.

The above discussed and many other features and attendant advantages of the present invention are detailed below. Other features and advantages of the invention will be apparent from the following description of the preferred embodiments thereof.

LEGENDS TO THE FIGURES

FIG. 1: In vivo electrotransfer in the rat eye.
A: Injection through a corneal tunnel in the ciliary muscle leading to the formation of a perilimbic bubble.
B: Intraocular electrode and perimibic extraocular electrode during the electrotransfer procedure.
C: Aspect of the electrotransferred site acutely after current application.
D: Picture of the annular periocular return electrode.

FIG. 2: GFP expression on transversal sections of the ciliary region after injection and electrotransfer of pEGFP-C1 plasmid.
A: Hematoxyllin-eosine histology showing the ciliary muscle (inset).
B: Higher magnification showing the longitudinal fibres (arrows) and the circular fibres (arrowheads).
C: Histochemistry of GFP localized in the ciliary muscle. Arrows indicate several highly GFP expressing tissue regions. Nuclei are stained with DAPI (several examples are indicated by circles).
D: Immunohistochemistry of alpha-smooth muscle actin showing the smooth fibres of the ciliary muscle. Arrows indicate several highly actin expressing tissue regions. Nuclei are stained with DAPI (several examples are indicated by circles).

FIG. 3: Localization of GFP expression on frontal sections of the ciliary region after injection and electrotransfer of pEGFP-C1.
A: Hemalun-eosine histology staining showing the circular fibres of the ciliary muscle.
B: Expression of GFP in the circular fibres of the ciliary muscle. Highly GFP expressing tissue regions are boxed. Nuclei are stained with DAPI (several examples are indicated by circles).

C: Expression of GFP in the longitudinal fibres of the ciliary muscle. Highly GFP expressing tissue regions are boxed. Nuclei are stained with DAPI (several examples are indicated by circles).
D: Immunohistochemistry of alpha-smooth muscle actin showing the smooth circular fibres of the ciliary muscle. Highly actin expressing tissue regions are boxed.
E: co-localization of alpha-smooth muscle actin and GFP demonstrating that expression of GFP is located in the ciliary muscle fibres. Co-localized expression regions demonstrated by the yellow fluorescence resulting from the addition of red and green fluorescence are boxed. Nuclei are stained with DAPI (several examples are indicated by circles).

Figure 4A:
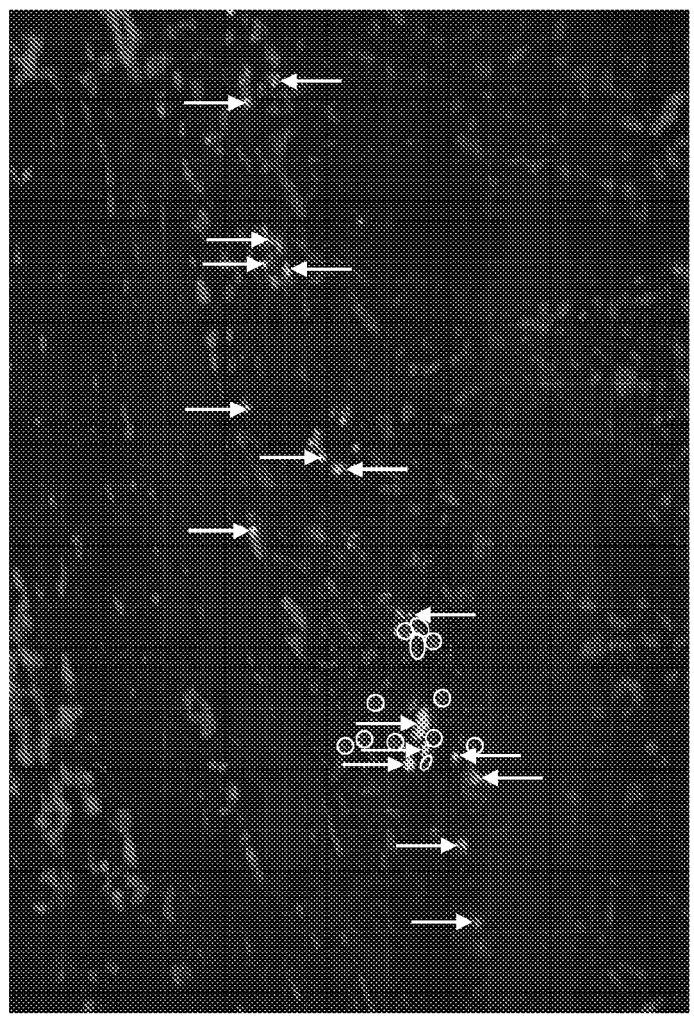
Figure 4B:
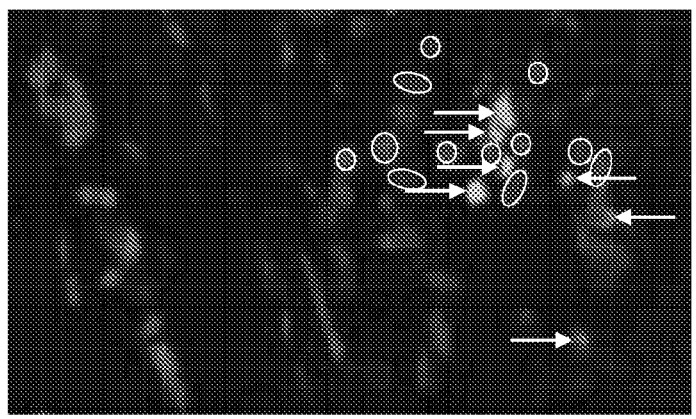

FIG. 4: Localization of GFP expression on frontal sections after injection of pEGFP-C1
A: Expression of GFP on few sparse cells of the ciliary body. Arrows indicate several highly GFP expressing tissue regions;
B: Higher magnification. Arrows indicate several highly GFP expressing tissue regions. Nuclei are stained with DAPI (several examples are indicated by circles).

Figure 5:
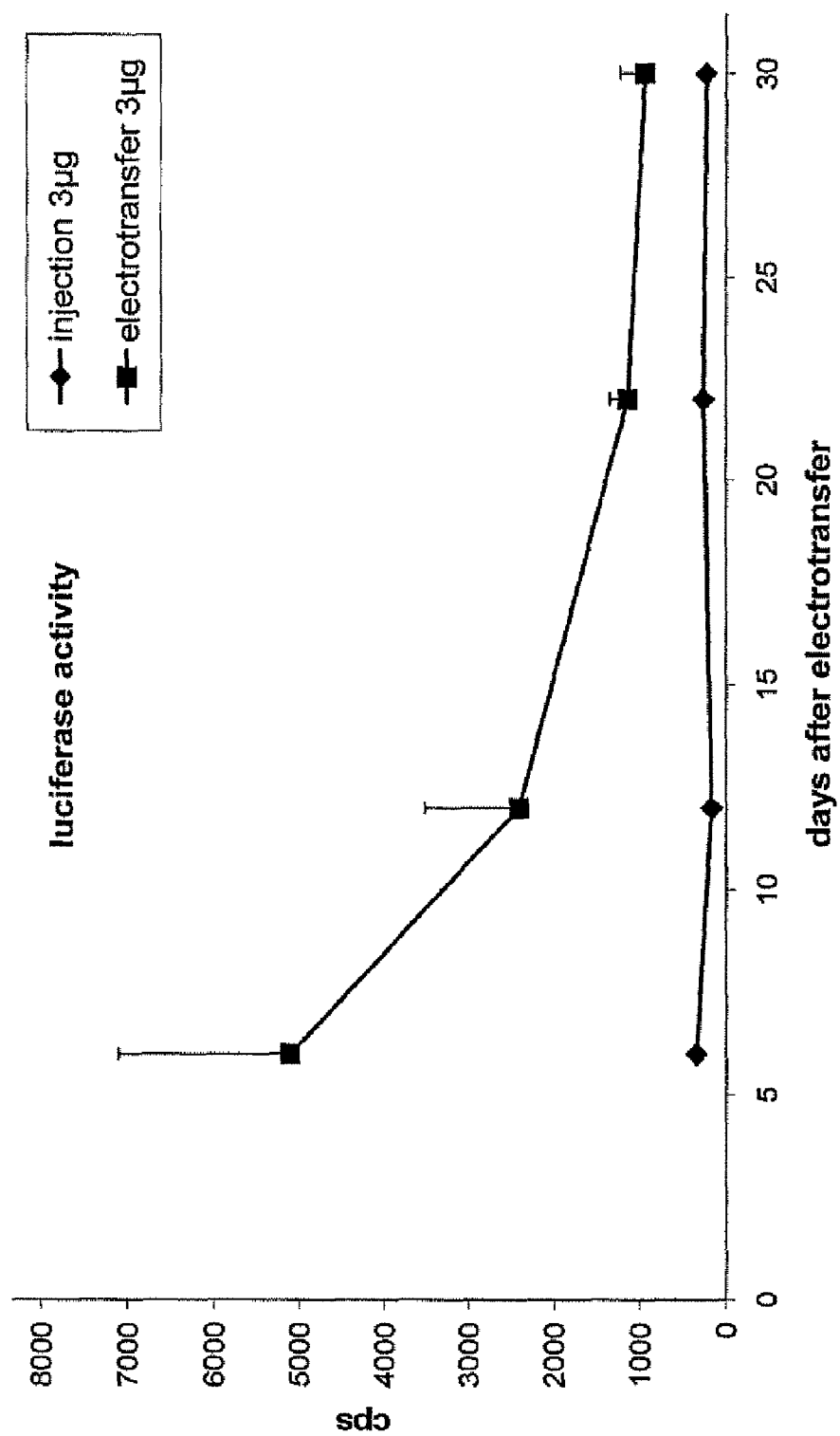

FIG. 5: Kinetics of LUC expression in the ciliary region
3 µg of plasmid pVAX2 luc were injected in the ciliary muscle of both eyes. The injection was followed by electrotransfer in the left eye of the rats. On day 6, 12, 22, and 30, six of the rats were sacrificed.

Figure 6:
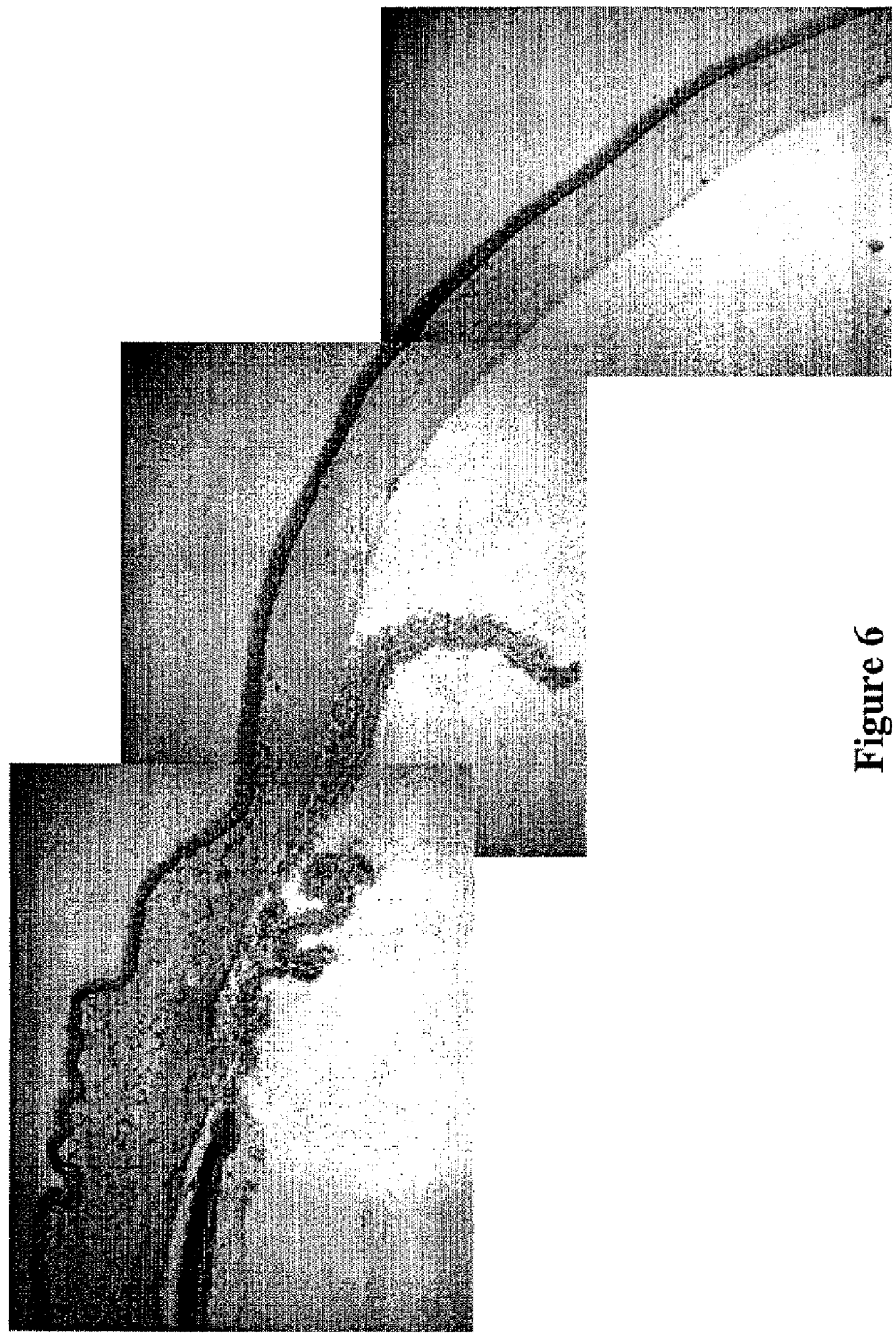

FIG. 6: Histology of the ciliary region 5 days after electrotransfer showing the integrity of ocular structures. Particularly, no cell infiltration and no granuloma is observed at the site of electroporation. 5 days post electro-transfer, no TUNEL positive cell was detected, showing the absence of apoptotic cells at this time point.

Figure 7:
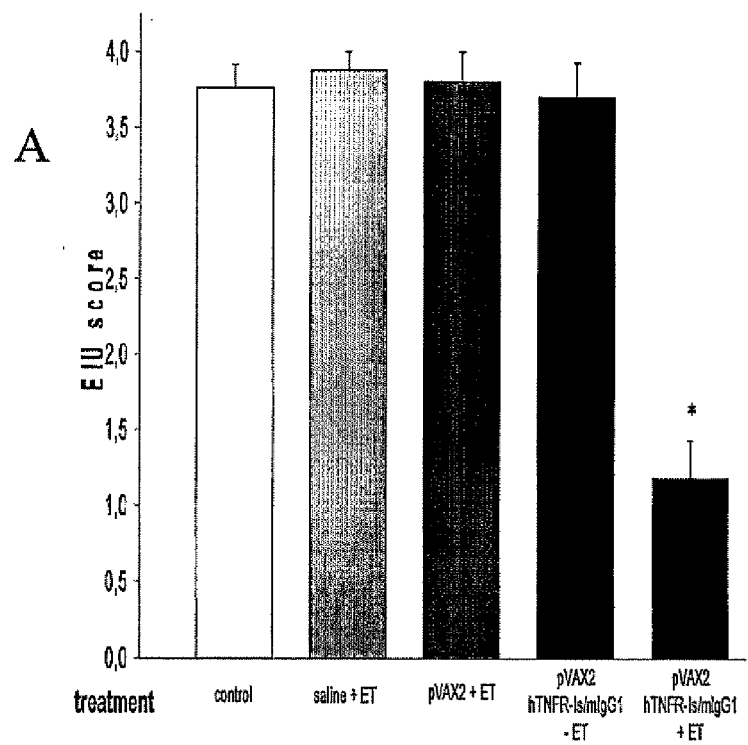
Figure 7:
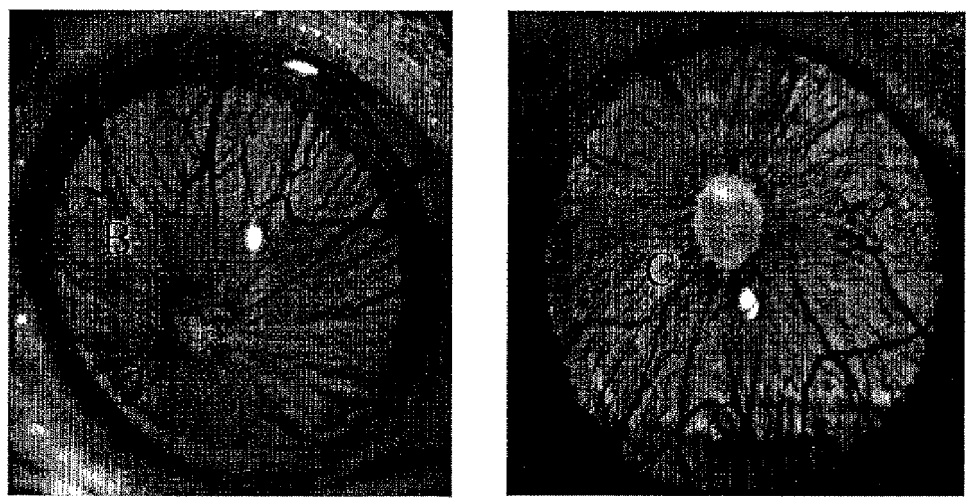

FIG. 7: Clinical scores of EIU
A: Clinical scores of EIU
Slit lamp photograph of an eye with EIU and without any treatment (B) (score 5), or after electro-transfer of 3 µg pEGFP-C1 GFP plasmid (C) (score 0).
*: $P<0.0001$ versus control or saline+ET or pVAX2+ET.

FIG. 8: Histology scores of EIU
A: Mean number of infiltrating cells in the anterior and posterior segments of the eyes with EIU after different treatment regimen.
**: $P<0.005$ versus control; †: $P<0.0002$ versus pVAX2+ET; ##: $P<0.0001$ versus pVAX2 hTNFR-Is/mIgG1–ET; *: $P<0.005$ versus control; #: $P<0.005$ versus pVAX2 hTNFR-Is/mIgG1–ET.
B-G: Microphotographs of eye sections from control rats (FIG. 8B: cornea) (FIG. 8C: iris/ciliary body), (FIG. 8D: optic nerve), and from rats treated with ET of 3 µg hTNFR-Is/mIgG1. (FIG. 8E: cornea), (FIG. 8F: iris/ciliary body), (FIG. 8G: optic nerve).

Figure 9:
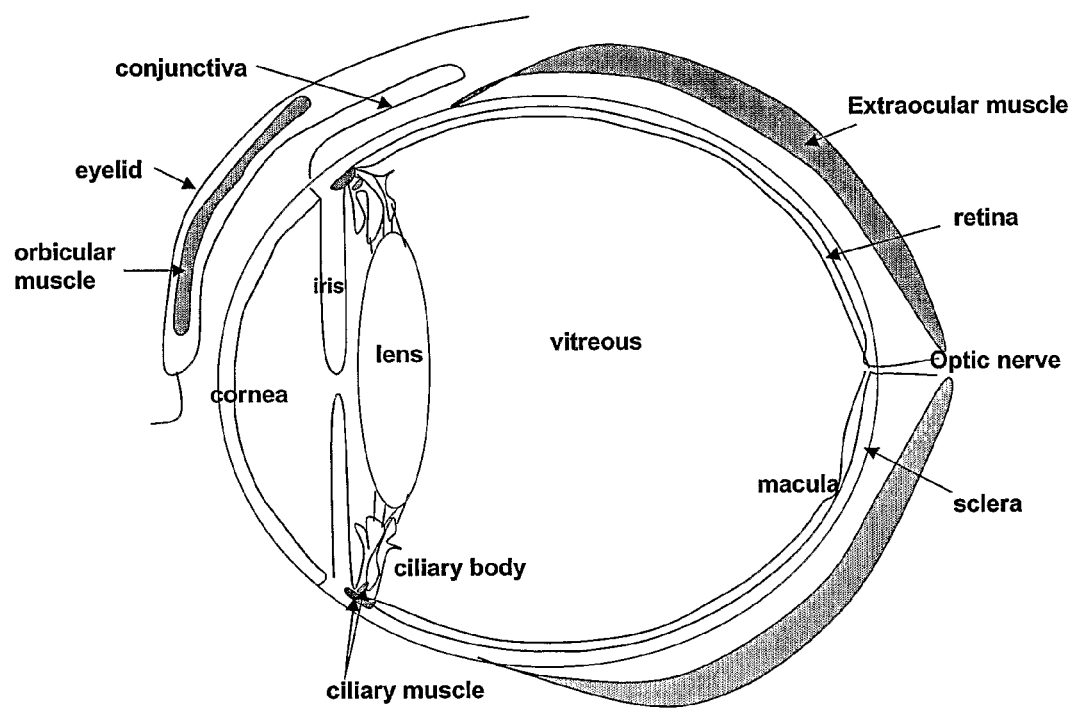

FIG. 9: Anatomy of the eye.

Figure 10:
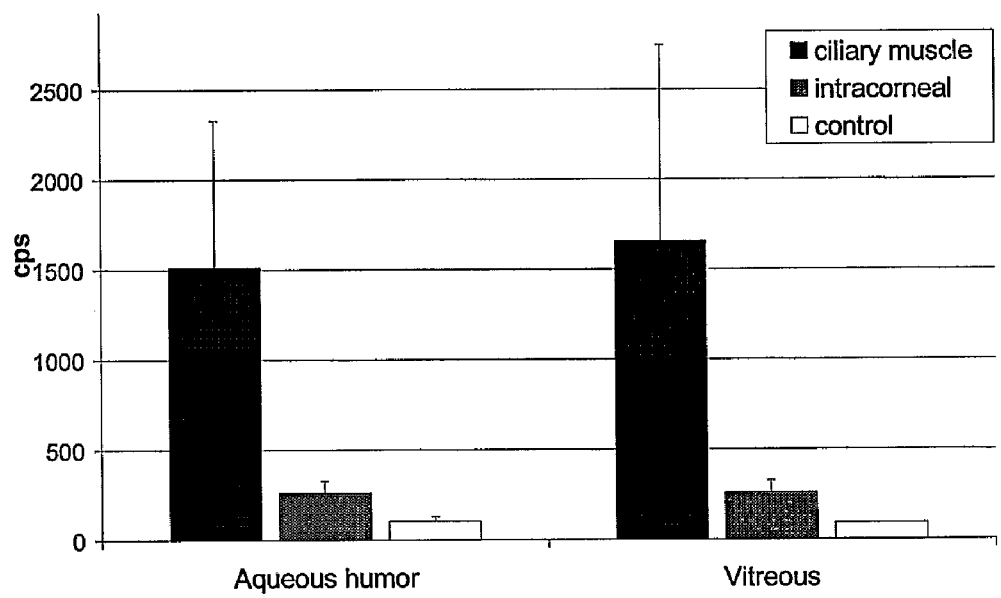

FIG. 10: Gaussia-luciferase (G-luciférase or Gluc) secretion rates, 7 days after injection and electrotransfer of the pCMV-Gluc plasmid (15 µg) into the ciliary muscle and into the cornea. The secretion rate is measured using a spectroscope measuring luminescence [expressed in count per second (cps)].

Figure 11:
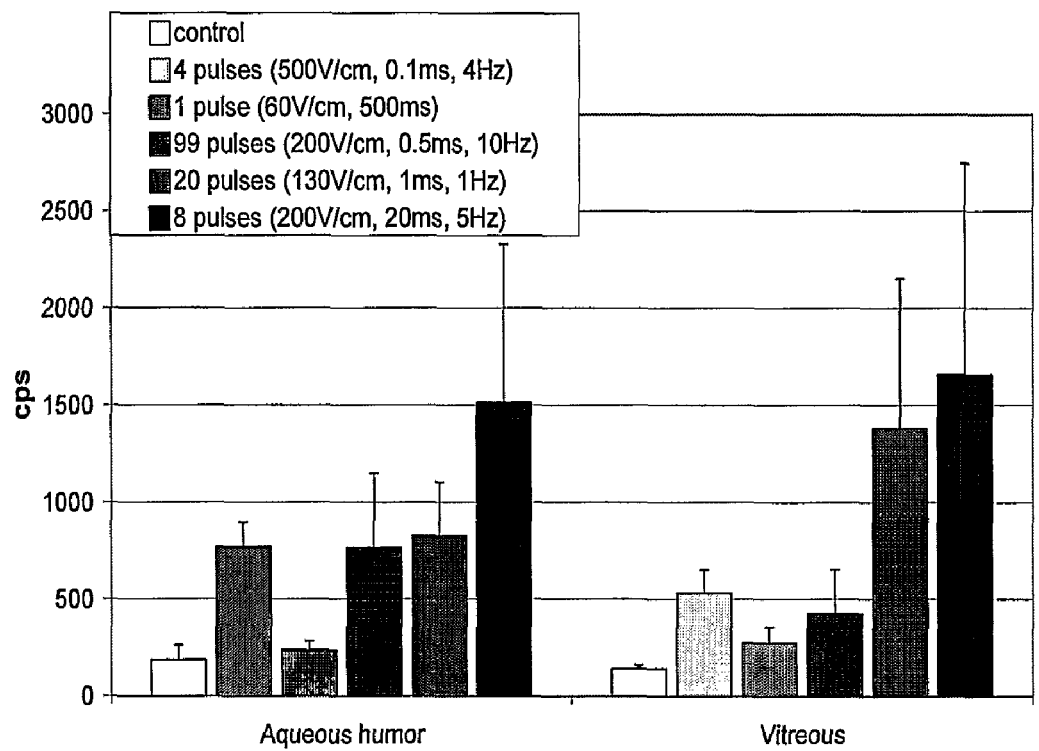

FIG. 11: Gaussia-luciferase (G-luciferase or Gluc) secretion rates, 7 days after injection and electrotransfer with various electric conditions (voltage, duration of pulses, number of pulses and frequency) of the pCMV-Gluc plasmid (15 µg) into the ciliary muscle. The secretion rate is measured using a spectroscope measuring luminescence [expressed in count per second (cps)].

Figure 12:
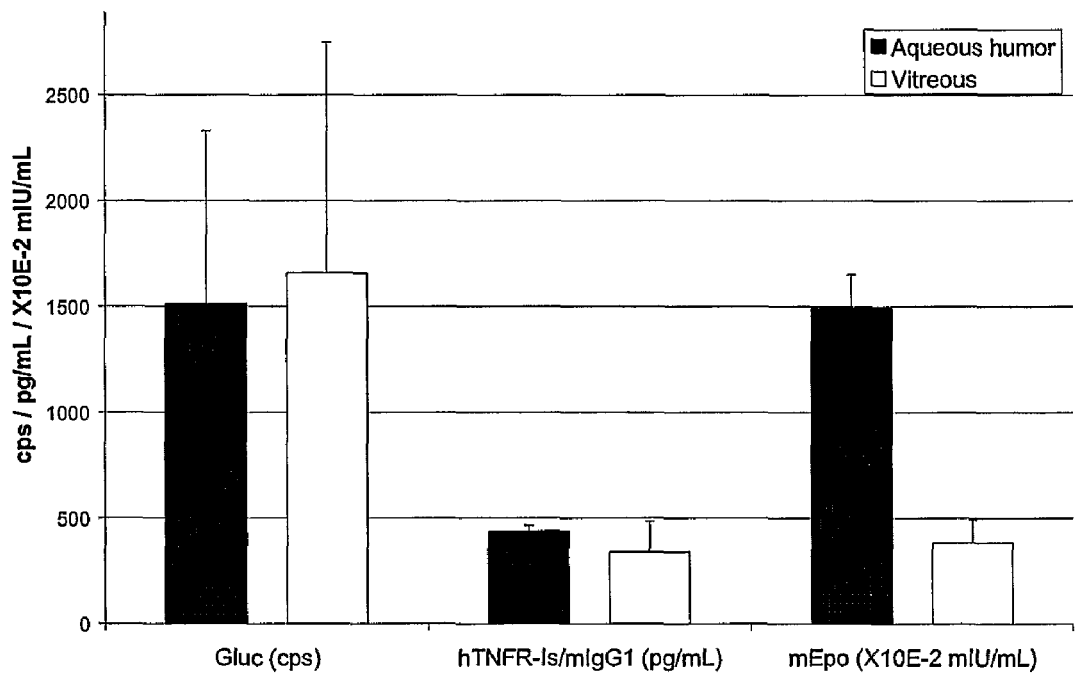

FIG. 12: Secretion of the Gaussia-luciferase (G-luciferase or Gluc), hTNFR-Is/mIgG1 and mEPO proteins in the aqueous humor and in the vitreous, 7 days after injection and electrotransfer of the plasmids expressing hTNFR-Is/mIgG1 and Gluc proteins (15 µg) and of the pVAX2mEpo plasmid (10 µg) into the ciliary muscle.

Figure 13:
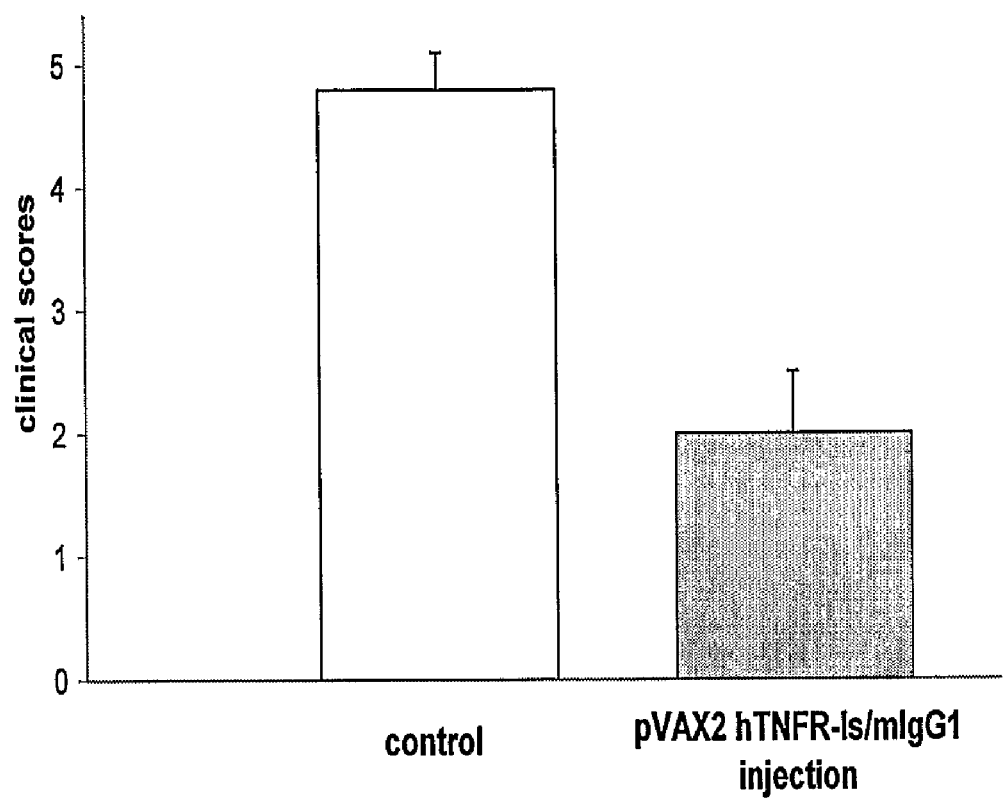

FIG. 13: Efficacy of the pVAX2 hTNFR-Is/mIgG1 plasmid (30 µg) on the clinical scores of endotoxin-induced uveitis (EIU) after injection (without electrotransfer) in the rat ciliary body. The injection of 30 µg of a TNFR-Is encoding plasmid in the ciliary body allows a 274±77 pg/ml TNFR-Is secretion rate in the aqueous humor.

Figure 14:
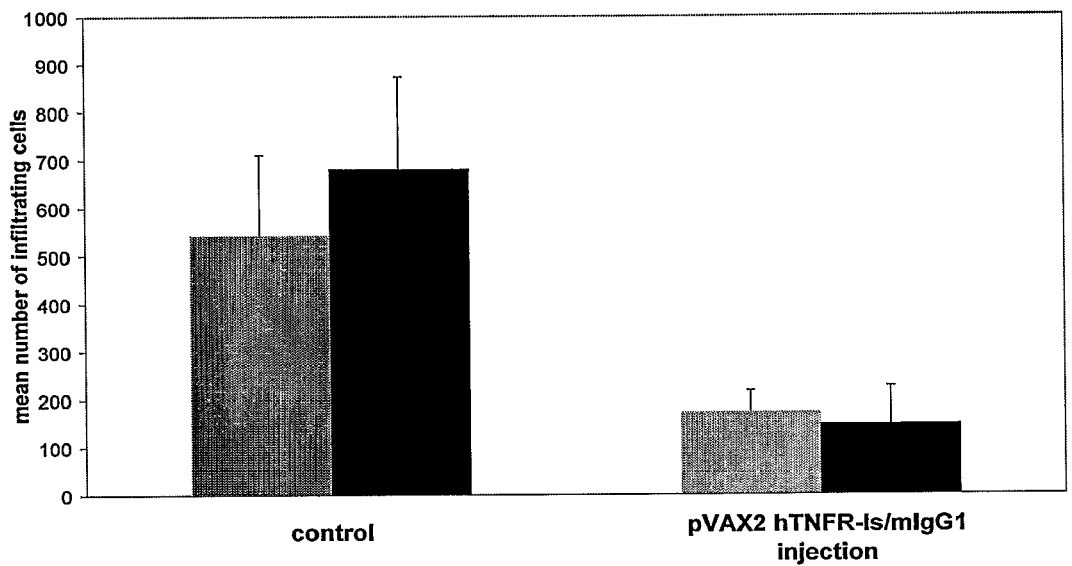

FIG. 14: Efficacy of the pVAX2 hTNFR-Is/mIgG1 plasmid (30 µg) on the histologic scores of endotoxin-induced uveitis (EIU) after injection (without electrotransfer) in the rat ciliary body, expressed in the mean number of infiltrating cells respectively in the anterior and posterior segments of the eye. The injection of 30 µg of a TNFR-Is encoding plasmid in the ciliary body allows a 274±77 µg/ml TNFR-Is secretion rate in the aqueous humor.

Figure 15:
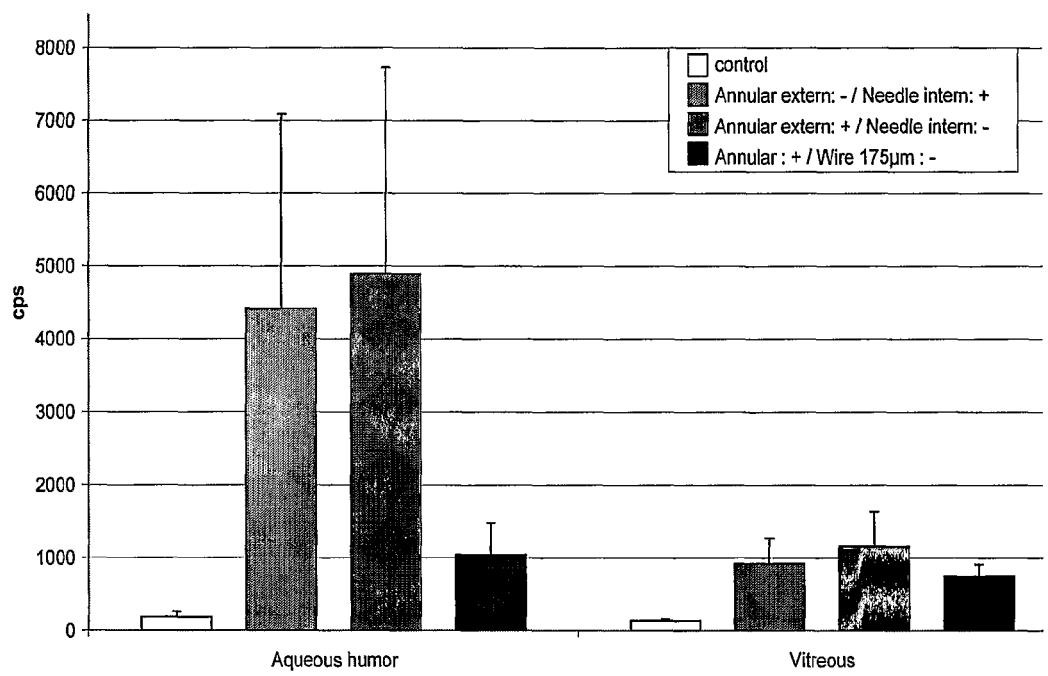

FIG. 15: Secretion of the Gaussia-luciferase (G-luciferase or Gluc) 7 days after injection and electrotransfer of the pCMV-Gluc plasmid (15 µg) into the ciliary muscle using various electrode devices comprising an annular means and a needle means or an annular means and a wire means. The electrical field applied is constituted of 8 electrical pulses, the field intensity of which is of 200 V/cm. The total duration of application of the electric field is of 20 ms for each pulse. The frequency is of 5 Hz. Inversion of polarity between electrodes does not modify the gene delivery efficacy.

Figure 16:
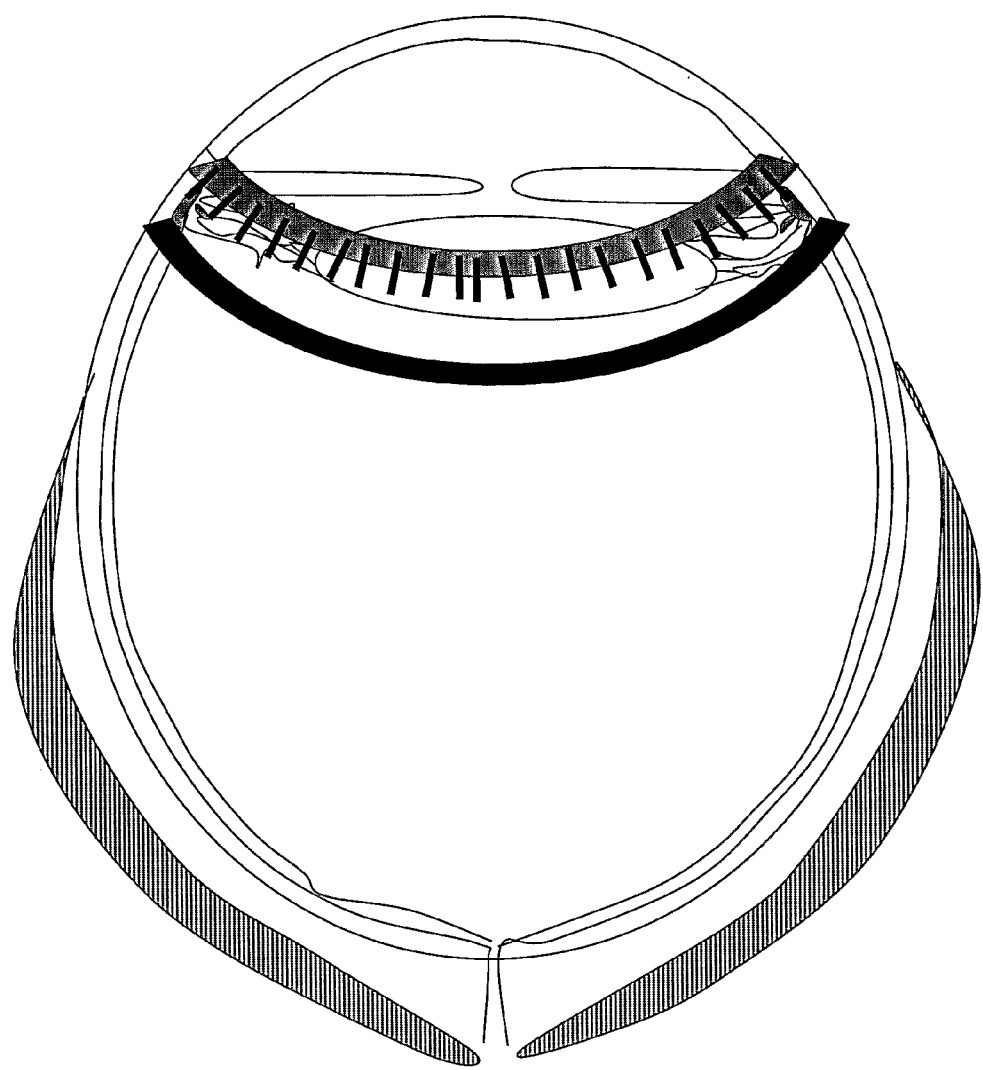

FIG. 16: Example of a ring-shaped device comprising two electrodes. Each tip of the comb-shaped first means (grey) may be used for injection and/or as an electrode. The second means (black) is an electrode which may be separated from the first means or may be bound up with it to get a fixed distance (between 2 and 5 mm) between the two means.

DETAILED DESCRIPTION OF THE INVENTION

The present invention describes a particularly efficient method for the selective transfer of a biologically active agent or product, in particular a nucleic acid, into ocular cells, in particular cells of the inner or posterior part of the eye. The invention demonstrates that it is possible to specifically transfer a nucleic acid into target ocular cells by administration into the ciliary body tissue(s) or cells (comprising the ciliary muscle, in particular the ciliary smooth muscle, and the ciliary epithelium) and/or to the extra-ocular muscle (comprising the orbicular muscle) tissue(s) or cells. Applicants describe herein that therapeutic or prophylactic products, in particular therapeutic or prophylactic nucleic acids, are advantageously administered at the level of the ciliary body tissue(s) or cells and/or the extra-ocular muscle tissue or cells, and distributed to the diseased ocular cells. Intra ciliary body tissue(s) or cells and/or intra extra-ocular muscle tissue or cells injections of a nucleic acid expressing a therapeutic or prophylactic product provides a particularly attractive mode of administration to deliver active agents to the ocular sphere. The invention indeed shows that nucleic acid administered to ciliary body tissue(s) or cells and/or to extra-ocular muscle tissue or cells will transduce said muscular cells, thus allowing the expression and/or secretion of the encoded product by said cells. Secretion allows a continuous release of the expression product in the vitreous body and/or into the aqueous humor (the ocular media) which will allow the treatment of desired intraocular tissues of the eye, preferably specific part(s) of the eye such as for example iris, ciliary body, retina, optic nerve or vitreous body itself of the eye. Intra ciliary body and/or intra extra-ocular muscle administration of the therapeutic or prophylactic nucleic acid leads to a large production and distribution of a therapeutic or prophylactic product within the eye, allowing high yield treatment of diseased ocular areas.

Intra ciliary body (ciliary muscle tissue or cells and/or epithelium or epithelial cells) and/or intra extra-ocular muscle administration of a therapeutic nucleic acid constitutes a new and very efficient method for treating the ocular cells. The present invention enables one to target the intra-ocular tissue on which it is desired to act, according to the location of the trauma and/or of the degeneration. In particular, the present invention advantageously enables one to target the cells of the different ocular tissues for example by adding a targeting sequence to the pharmacological product. The present invention has been found to be less traumatic and more specific than stereotaxic injection into the forehead (optionally until the level of the eye ball) which is more diffuse and not restricted to the ocular sphere. The present invention is also much more efficient as it allows a continuous and/or targeted production of the desired therapeutic product in vivo compared to direct administration of said product for example in the vitreous body.

One object of the invention thus relates to the use of a biologically or pharmacologically active agent, preferably a therapeutic or prophylactic nucleic acid, for preparing a composition for the treatment or prevention of an ocular disease by administering said composition to the ciliary body tissue (s) or cells and/or to the extra-ocular muscle tissue or cells of the subject to be treated.

When the ciliary epithelium is specifically transfected, it is used to produce translated proteins or peptides that are able to regulate the production of aqueous humor, particularly for the treatment of elevated intraocular pressure. In the case of transfection in the ciliary epithelium, the peptide or translated proteins are designed to regulate the production of aqueous humor locally and local administration is therefore needed in such a case.

Administration

While a significant knowledge has been accumulated over the years, as indicated previously, many problems are often associated with the in vivo administration of products, in particular peptides, proteins and nucleic acid, into eukaryotic cells by conventional methods. Typically, peptides, proteins, small nucleic acids such as aptamers or antisense oligonucleotides have to be frequently injected using invasive needles for obtaining a therapeutic effect. Similarly, when delivering DNA for transfection, only a small percentage of target cells to be transfected with the heterologous nucleic acid actually express at satisfying levels the product of interest, notably the mRNA or protein of interest transcribed and translated from the transfected transgene. In addition, some therapeutic compositions, such as those that include synthetic oligonucleotides, are very expensive, toxic and degradable, and, consequently, require very localized application, efficient internalization into the target cells, and frequent administrations. Finally, it might be advantageous to deliver locally a protein with undesirable general toxicity risk such as a cytokine, an antibody, an anti-cytokine such as anti-TNFα soluble receptors, or other proteins from current art. For instance, systematically administered anti-TNFα soluble receptor has been shown to increase the risk of tuberculosis.

The methods and uses according to the present invention are designed to induce a prolonged local expression of any biologically active product or agent. Applicants describe herein that the administration of a biologically active agent, in particular a therapeutic or prophylactic nucleic acid, or a composition comprising such an agent, into the ciliary body tissue(s) or cells and/or into the extra-ocular muscle tissue or cells, causes the ciliary body tissue(s) or cells and/or the extra-ocular muscle tissue or cells to produce or secrete an agent at physiological and/or therapeutic or prophylactic doses. The muscular expression product may for example be distributed to the diseased ocular cells by a continuous release in the vitreous body and/or the aqueous humor.

An object of the present invention thus relates to the administration of a biologically active agent, in particular a therapeutic or prophylactic nucleic acid, or a composition according to the invention comprising such an agent, to the ciliary body tissue(s) or cells and/or to the extra-ocular muscle tissue or cells of the subject to be treated.

The biologically active agent, in particular a nucleic acid, or the composition according to the invention may be administered for example by transconjunctival, transscleral, transcorneal, intraocular (preferably during surgery) or endoscopic route. Injection can be performed during vitrectomy in combination or not with surgical gaz infusion. Administration may be performed by a unique injection site or at multiple injection sites.

In a preferred embodiment of the present invention, the administration is performed directly into the ciliary body tissue(s) or cells and/or into the extra-ocular muscle tissue or cells, and includes preferably an injection step of the biologically active agent into said muscle(s). Such a direct injection may be performed by transconjuntival, transscleral or transcorneal route.

The direct administration or transfer into the ciliary body tissue(s) or cells and/or into the extra-ocular muscle tissue or cells may be performed using a number of techniques, such as by electroporation, by surgical treatment, by thermal treatment, by iontophoresis, by sonophoresis, by using pneumatically delivered biologically active agent-coated particles such as gold particles used in a "gene gun". With a particle bombardment device, or "gene gun", a motive force is generated to accelerate coated high density particles (such as gold or tungsten) to a high velocity that allows penetration of the eye tissues or cells.

In a preferred embodiment of the present invention, administration is realized by electroporation, also and indifferentially designated here by the term "electrotransfer", or comprises an electroporation step, in addition to the injection step. Electroporation comprises the application of an electric field as will be described in more details later in the application.

It has been found by inventors that mechanical or physical injection of biologically active nucleic acids into the ciliary body tissue(s) or cells and/or into the extra-ocular muscle tissue or cells yields a high percentage of cells which are transfected and have sustained marker expression.

Non direct administration may be performed instead of or in addition to anyone of the above mentioned methods. Non direct administration usually comprises injection of the pharmaceutical product into a body fluid such as the bloodstream, the pharmaceutical product advantageously comprising an addressing signal sequence to the ciliary body tissue(s) or cells or to the extra-ocular muscle tissue or cells. Non direct administration may be performed using a cellular receptor-based endocytosis method or using chemical mediated uptake.

In the receptor-based endocytosis method, a ligand (specific to a cell surface receptor) is made to form a complex with the pharmaceutical product, preferably a nucleic acid of interest. The complex is then injected into a body fluid such as the bloodstream of the subject. Target cells that have the cell surface receptor will specifically bind the ligand and transport the ligand-product complex into the cell.

Chemical mediated uptake may be a calcium phosphate transfection or may involve the use of fusogenic lipid vesicles such as liposomes or other vesicles for membrane fusion. A carrier harboring the pharmaceutical product of interest, preferably a nucleic acid of interest, can be conveniently introduced into a body fluid and then site specifically directed to the ciliary body tissue(s) or cells and/or to the extra-ocular muscle tissue or cells. Ciliary body tissue(s) or cells and/or extra-ocular muscle tissue or cells-specific therapeutic or prophylactic product-carrying liposomes, for example, can be developed and the product carried by the liposome absorbed by those specific cells. Injection of immunoliposomes that are targeted to a specific receptor on ciliary body tissue(s) or cells and/or on extra-ocular muscle tissue or cells can be used as a convenient method of inserting the therapeutic or prophylactic product into the ocular muscle cells bearing that receptor.

Either the mechanical, physical or chemical delivery to the ciliary body tissue(s) or cells and/or to the extra-ocular muscle tissue or cells, or a combination of these different methods may involve the preliminary use of enzymes such as hyaluronidase, dispase, alpha chimotrypsin, etc., which will enhance drug diffusion in the ciliary body tissue(s) or cells and/or in the extra-ocular muscle tissue or cells, and will eventually enhance cellular uptake.

Once within the cells, the nucleotide sequences can be made to produce the therapeutic substance within the cellular or nuclear (nucleus) environments (either episomal or after chromosomal integration). Nuclear incorporated nucleotide sequences can produce, as explained above, the therapeutic product for extended periods including permanently.

The desired therapeutic or prophylactic product may also be re-administered periodically to maintain the product level, for example, when the product is a nucleic acid, to maintain the level of nucleic acids without mutation occurring in the recipient ciliary body tissue(s) or cells and extra-ocular muscle tissue or cells.

Electroporation

Among the methods allowing or enhancing the in vivo transfer of nucleic acids into target cells, electroporation can be particularly cited. Electroporation means are responsible for, or increase, permeability of a cell membrane and/or at least a portion of a targeted tissue to a biologically active agent such as a nucleic acid. In addition, a brief electric impulse with a given field strength is used to allow transport or migration of agents through the tissue or across cell membranes into cells, by an electrophoretic effect. The technique of electroporation is well known to those of ordinary skill in the art.

This method works on the principle that cells act as an electrical capacitor generally unable to pass current. Subjecting the cells to an electric field creates transient permeable structures or micropores in the cell membrane. The pores are large enough to allow the pharmaceuticals and/or nucleic acid to gain access to the cells. As a result of the "pores" briefly formed in the cell membrane, the biologically active molecules initially enter the cytoplasm or the nucleus in which they can already exert their function to be studied if necessary. With time, the pores in the cell membrane close and the cell once again becomes impermeable. In addition to the pore effect, the polyanionic, electrically charged nucleotide is also driven into tissue and cells by the electrophoretic effect of the applied electrical pulses.

In the present application, applicants demonstrate that the biologically active agent transfer into ciliary body tissue(s) or cells and/or into the extra-ocular muscle tissue or cells may be allowed or increased by applying desired ocular tissue(s) an electrical field constituted of one or more electrical pulse(s), the field intensity of which is between about 1 and 600 volts/cm, preferably 1 and 400 volts/cm, even more preferably between about 50 and 200 volts/cm, advantageously between about 50 and 150 volts/cm, 75 and 150 volts/cm or 50 and 100 volts/cm. A particularly preferred electrical field intensity usable in the present invention is an intensity of 200 volts/cm.

The total duration of application of the electric field may be between 0.01 millisecond and 1 second, preferably between 0.01 and 500 milliseconds, more preferably between 1 and 500 milliseconds, even more preferably greater than 1 or 10 milliseconds. In a preferred embodiment, the total duration of application of the electric field is between 10 milliseconds and 100 milliseconds and is preferably of 20 milliseconds.

Electric pulses applied may be between for example 1 and 100 000. Their frequency may be comprised between 0.1 and 1000 hertz. It is preferably a regular frequency.

Electric pulses may also be delivered in an irregular manner relative to each other, the function describing the intensity of the electric field as a function of the time for one pulse being preferably variable.

The delivered electric field may be for example the combination of at least a first electric field greater than 400 volts/cm of less than 1 millisecond and one or more electric pulses of less than 400 volts/cm and about 1 millisecond. The delivered electric field may further be for example the combination of at least a first electric field greater than 200 volts/cm of less than 1 millisecond and one or more electric pulses of less than 200 volts/cm and about 1 millisecond.

The integral of the function describing the variation of the electric field with time is preferably greater than 1 kV×msec/cm, even more preferably greater or at least equal to 5 kV×msec/cm.

In a preferred embodiment, the electric field applied to the tissue or cells comprises between 1 and 10 pulses, preferably 8 pulses, of frequency between 1 and 10 Hz, preferably of 5 Hz.

Electric pulses may be unipolar or bipolar wave pulses. They may be selected for example from square wave pulses, exponentially decreasing wave pulses, oscillating unipolar wave pulses of limited duration, oscillating bipolar wave pulses of limited duration, or other wave forms. Preferentially, electric pulses comprise square wave pulses or oscillating bipolar wave pulses.

In a particular embodiment of the invention, the administration comprises an electroporation step implying the application, to the tissue(s), of an electric field comprising 8 unipolar square wave pulses, of frequency of 5 Hz, the intensity of each pulse being of 200 volts/cm for a total duration of application of the electric field of 20 ms per pulse.

Electroporation is typically carried out by applying voltage pulses between a pair of electrodes which are applied to the tissue surface. The voltage must be applied in proportion to the distance between the electrodes. When the distance between the electrodes is too great, the generated electric field penetrates deep into the tissue where it causes unpleasant nerve and muscle reaction.

In the present invention, the electrical pulses are preferably to be applied using at least two electrodes distant from each other by less than one centimetre, at least one of said electrodes being introduced into the ciliary body tissue(s) or cells or into the extra-ocular muscle tissue or cells. Preferably, at least one of said electrodes is applied on the surface of the sclera or eye conjunctiva, preferably the limbic conjunctiva.

Electrodes are preferably distant from each other by less than 10 millimetres, more preferably by less than 9, 8, 7, 6, 5, 4, or 3 millimetres, even more preferably by less than 2 millimetres or 1 millimetre.

In the above described use according to the present invention, a iontophoresis step may be performed before, during or after the electroporation step, preferably before said step. Iontophoresis consists in the administration of a product into the body through the tissues using an electric field involving a small current density (such as for example a density which is between 0.5 and 2 mA/cm$^2$). An electrode is arranged at the site to be treated while a second electrode, intended to close the electric circuit, is placed at another site on the body. These iontophoresis voltage ranges from 0.001 to 40 V/cm, and last from several seconds to several hours (for a transpalpebral iontophoresis), preferably to 10 minutes, even more preferably to 7 minutes or to 5 minutes (when iontophoresis is applied directly to the eye).

Devices for transdermal, transcutaneous delivery of therapeutic agents through iontophoresis are commonly used for treating skin or eye diseases, and thus have been already disclosed. So, the skilled artisan could easily choose and determined the iontophoresis device and its use conditions, particularly the current density, the period of time of applying the current and the electrodes form and location etc., adapted to the ocular tissue containing the target cells. Among the iontophoresis devices which can be used for intraocular delivery of biologically active agent, preferably nucleic acid, as defined above, in the method according to the present invention, the iontophoresis system disclosed in the patent document U.S. Pat. No. 6,154,671 is preferred.

Device

The present invention also relates to a device which may be used in a delivery method according to the invention. In a particular embodiment, said method is constituted by or comprises an electroporation step. Such electroporation step is however not compulsory to achieve the injection of a composition according to the invention in the ciliary body tissue(s) or cells or in the extra-ocular muscle tissue, in conditions adapted to therapy.

An object of the present invention thus relates to an electroporation device for administering a composition to the ciliary body tissue(s) or cells and/or to the extra-ocular muscle tissue or cells of a subject, comprising:
(i) at least one means for injecting the composition into said tissue(s) or cells, wherein said injection means is an injection needle, an injection needle electrode, a microneedle array comprising at least one injection needle or one injection needle electrode, or a combination thereof,
(ii) optionally, a means for sensing when the needle has been inserted to a sufficient depth for injection of the composition to commence, said depth being comprised between 0.1 and 10 mm, preferably 0.2 and 0.9 mm (advantageously this depth is of about or strictly 0.5 mm),
(iii) optionally, a means to position said injection means on the surface of the sclera or eye conjunctiva, and
(iv) optionally, a means for generating a predetermined electric signal.

The means to inject the composition may be an injection needle, an injection needle electrode, a microneedle array comprising at least one injection needle or one injection needle electrode, or a combination thereof. Holes can be provided along the length of the injection needle(s) and/or injection needle electrode(s) as well as at the end thereof to improve the distribution of injected substances. Further, one or more of the injection needles and/or injection needle electrodes may be hollow and can include openings through which the therapeutic or prophylactic agent can be injected into the ciliary body tissue(s) or cells and/or into the extra-ocular muscle or cells. Alternatively, the means to inject the composition might be any means familiar to the experimentator skilled in the art, such as a gene gun device, a catheter, etc.

The length of the injection needle or injection needle electrode may be comprised between 0.1 mm and 4 cm (for example 3, 2 or 1.5 cm). The length of the injection needle or injection needle electrode part penetrating the target tissue (ciliary body tissue(s) or extra-ocular muscle tissue) is advantageously comprised between 0.1 mm and 2 cm, preferably between 0.1 mm and 10 mm, even more preferably between 0.2 and 0.9 mm (for example 3, 4, 5, 6, 7 or 8 mm). The length of the injection needle or injection needle electrode is preferably comprised between about 0.1 and 0.9 mm (for example 0.2, 0.3, 0.4, 0.5, 0.6, 0.7 or 0.8 mm) and is preferably of about or strictly 0.5 mm.

The device may further comprise a means for sensing when the needle has been inserted to a sufficient depth for injection of the composition to commence, said depth being comprised between 0.1 and 10 mm, preferably 2 and 9 mm. For example this depth is of about or strictly 0.2, 0.3, 0.4, 0.5, 0.6, 0.7, 0.8, 0.9, 1, 2, 3, 4 or 5 mm.

One can choose when to commence injection of the composition according to the invention. Ideally, injection is commenced when the tip of the needle has reached the ciliary body tissue of interest (muscle or epithelium) or the extra-ocular muscle tissue and the device preferably includes a means for sensing when the needle has been inserted to a sufficient depth for injection of the composition to commence. This means that injection of the composition can be prompted to commence automatically when the needle has reached a desired depth (which will normally be the depth at which muscle tissue begins). The depth at which muscle tissue begins could for example be taken to be a preset needle insertion depth comprised between 0.1 and 10 mm, preferably 2 and 9 mm. For example this depth may be of about or strictly 0.2, 0.3, 0.4, 0.5, 0.6, 0.7, 0.8, 0.9, 1, 2, 3, 4 or 5 mm which would be deemed sufficient for the needle to get through the sclera or eye conjunctiva.

In one preferred embodiment the sensing means comprises an ultrasound probe.

In an alternative preferred embodiment the sensing means comprises means for sensing a change in impedance or resistance. In this case, the means may not as such record the depth of the needle in the body tissue but will rather be adapted to sense a change in impedance or resistance as the needle moves from a different type of body tissue into the eye.

The depth of insertion of the needle can further be recorded if desired and could be used to control injection of the composition such that the volume of composition to be injected is determined as the depth of needle insertion is being recorded.

The device described above could be used for any type of injection. It is however envisaged to be particularly useful in the field of electroporation and so it preferably further comprises means for applying a voltage to the needle in particular for generating a predetermined electric signal. This allows the needle to be used not only for injection but also as an electrode during electroporation. This is particularly advantageous as it means that the electric field is applied to the same area as the injected composition.

In a preferred embodiment, the injection device comprises at least two electrodes distant from each other by less than one centimetre, at least one of said electrodes being of a polarity different from that of the other electrode(s). Advantageously, at least one of said at least two electrodes is an injection means as defined previously.

Electrodes are preferably chosen from a wire type electrode and a plate contact type electrode, each type of electrode being optionally adapted to be reversibly applied on the surface of the sclera or eye conjunctiva, preferably the limbic conjunctiva (for example when they are at least partly ring-shaped).

In a first embodiment, the wire type electrode may be introduced transconjunctivally and transsclerally in the eye, for example in the unique tunnel or in one of the tunnels made while injecting the composition, preferably at a distance of several millimetres, preferably comprised between 1.5 and 4 mm from the limbus (even more preferably at a distance of 2.5 mm of the limbus in the adult eye). The wire is for example introduced parallel to the limbus. The wire may then penetrate into the ciliary body on a distance comprises between about 2 and 10 mm. Such a wire electrode may be used with at least one plate contact type electrode or with at least another wire electrode (for example ring-shaped) or with a combination thereof. A ring-shaped electrode may for example be used as a return electrode and be introduced through the cornea, around the limbus, for example at a distance, comprised between 1 and 9 millimetres, from the intra-ocular wire electrode(s). Two or more electrodes are preferably simultaneously used.

When two electrodes only are used and are, for example, both ring-shaped electrodes, one electrode can cover the other one without inducing any adverse effect.

The wire type electrode used in the way described above is advantageous as it is less invasive than other electrode types and is further easy to use. The wire electrode also allows the increase of the electrical surface of the electrode and thus lead to a better transgene expression.

In a second embodiment, the shape of the wire type electrode is that of a ring or part thereof. Such a wire is advantageously adapted to be reversibly applied on the surface of the sclera or eye conjunctiva, preferably the limbic conjunctiva.

The length of the wire electrode may be comprised between 1 millimetre and 3 centimetres, preferably between 1 and 10 millimetres. The wire electrode will be longer (of 5, 3 centimetres or less) when it is ring-shaped. It will of course be shorter (for example 1, 2, 3, 4 or 4 millimetres) when adapted to be introduced transsclerally.

The plate contact type electrode may be curved or not. It may also be designed or not like a comb comprising at least two tips (preferably from 3 to 20 tips, for example 4, 5, 6, 7, 8, 9, 10, 11, 12, 13, 14, 15, 16, 17, 18 or 19 tips), at least one of said tip comprising the injection means of the device. The width of the wire electrode is preferably inferior to about 1 centimetre, preferably inferior to 0.5 millimetres.

In a particular embodiment, the plate-contact electrode is preferably made of a rigid material and of a curved form adapted to the geometry of the surface of the sclera or eye conjunctiva.

In a further embodiment, the plate-contact electrode is preferably made of a flexible material adapted to the geometry of the surface of the sclera or eye conjunctiva.

The at least two electrodes are preferably distant by less than 1.5 or 1 centimetre, even more preferably by less than 15 or 10 millimetres, preferably less than 14, 13, 12, 10, 9, 8, 7, 6, 5, 4, 3 or 2 millimetres. The distance between each electrodes is advantageously of 1 millimetre or even less.

When the device comprises at least two electrodes, said electrodes may be independent or connected together.

Electrodes are advantageously made of a conductive non oxidative metal selected for example from iridium or platinum.

The device according to the invention may advantageously comprise a means to position and/or maintain the previously described injection means on the surface of the sclera or eye conjunctiva before and during injection. The positioning means is advantageously adapted to be reversibly applied on the surface of the sclera or eye conjunctiva, preferably the limbic conjunctiva.

The positioning means may be reversibly connected to the injection means. It may further be connected to at least one electrode and/or to the means for sensing when the needle has been inserted to a sufficient depth in the eye.

The positioning means may be a ring-shaped means or part thereof. It can be made of a rigid material and be of a curved form adapted to the geometry of the surface of the sclera or eye conjunctiva or it can be made of a flexible material adapted to the geometry of the surface of the sclera or eye conjunctiva.

In a particular embodiment, the positioning means of the device according to the invention is designed like a comb, which may be curved, comprising at least two tips, at least one of said at least two tips comprising an injection means as described previously.

The internal diameter of the ring-shaped positioning means is preferably comprised between 10 and 20 mm, even more preferably between 13 and 14 millimetres and the external diameter of the ring-shaped positioning means is preferably comprised between 15 and 25 millimetres, even more preferably between 15 and 16 millimetres.

The length of the tips is preferably comprised between 0.1 mm and 3 or 1 mm, preferably 0.4 mm and 0.8 mm, and is even more preferably of 0.5 mm.

The angles between the ring-shaped means, or part thereof, and the tips may vary depending on the depth of injection required and may be comprised between 1° and 90°, for example 5°, 10°, 20°, 30°, 40°, 50°, 60°, 70° and 80°.

In a particular embodiment, the positioning means of the device according to the invention may also have a plurality of bores through which a plurality of injection needles and/or needle electrodes extend, the bore corresponding to the needle electrodes being separately connected to a conductor so that each of the electrodes can be connected to a power supply in use. An insulating portion can be provided along the midportion of each electrode so as to isolate the body tissue adjacent the insulated part of the needle from the electric field produced by the electrode in use.

In another particular embodiment, the positioning means of the device according to the invention may be ring-shaped and have electrodes inserted at both sides of the ring. A first set of electrodes may then be used as injecting means and simultaneously as positive or negative electrodes while the remaining electrodes (second set of electrodes) are of a polarity different from that of the first set of electrodes. Both set of electrodes may be inserted in the ciliary body (in particular in the ciliary muscle). The distance between the electrodes is preferably comprised between 10 and 20 millimetres, even more preferably between 12 and 17 millimetres. In this particular case, there is no need to further use a plate-contact-return electrode.

A particular device according to the invention comprises:
(i) at least one means for injecting the composition into said tissue(s) or cells, wherein said injection means is a microneedle array comprising at least two injection needle electrodes,
(ii) optionally, a means for sensing when the needle(s) has (have) been inserted to a sufficient depth for injection of the composition to commence, said depth being comprised between 0.1 and 10 mm, preferably 2 and 9 mm (advantageously this depth is of about or strictly 0.7 or 0.5 mm),
(iii) a means to position said injection needle electrode or microneedle array on the surface of the sclera or eye conjunctiva, said positioning means being ring-shaped and designed like a comb comprising at least two tips, said tips each comprising one of the at least two injection needle electrodes, and (iv) a means for generating a predetermined electric signal.

In a device, such as the one described above, the unique array of electrodes used is the injection means, electric pulses may be delivered using a power supply (means for generating an electric signal) giving alternate polarity from one electrode to the next one respectively comprised in each tip of the comb.

The device may further comprise a pipe system for infusion of the composition.

The administered composition comprises a biologically active agent, preferably a therapeutic or prophylactic nucleic acid, or a composition according to the invention as described previously in the application.

Administration being realized in vivo, it may sometimes be useful to use intermediary products able to ensure an electric continuity with the external non invasive electrode(s). It may be for example electrolytes such as those used to prepare a composition according to the invention and mentioned above.

The present invention at least in its preferred embodiments seeks to provide a device which can be used in vivo in particular in gene therapy.

Pharmacologically Active Agent

The present invention relates to the discovery that ciliary body tissue(s) or cells and/or extra-ocular muscle tissue or cells administration provides a means for delivering a pharmacologically active agent to ocular tissue(s) or cells.

Such agents may be either naturally occurring or non-naturally occurring. A non-naturally occurring molecule may for example be an artificial, synthetic, chimeric or truncated molecule.

As used herein, a naturally occurring molecule may be "substantially purified", if desired, such that one or more molecules that is or may be present in a naturally occurring preparation containing that molecule will have been removed or will be present at a lower concentration than that at which it would normally be found.

The therapeutic products or pharmacologically active agents, as used herein, comprise biologically active organic molecules, selected for example from nucleic acid molecules, proteins and any derivative or part thereof. These agents can be of artificial or synthetic (notably biosynthetic) origin, or be extracted from a virus (AAV or ADV for example) or from a unicellular or pluricellular eukaryotic or prokaryotic organism. They may be for example of human origin, other mammalian, plant, bacterial or viral origin or may be derivatives thereof which retain the desired biological effect.

The agents of the present invention will indeed preferably be "biologically active" with respect to either a structural attribute, such as the capacity of a nucleic acid to hybridize to another nucleic acid molecule, or the ability of a protein to be bound by antibody (or to compete with another molecule for such binding). Alternatively, such an attribute may be catalytic, and thus involve the capacity of the agent to regulate, mediate or induce a biological or chemical reaction or response, either prophylactic or therapeutic.

The term "derivative", as used herein, refers to the chemical modification of a polypeptide or a polynucleotide sequence.

Chemical modifications of a polynucleotide sequence can include, for example, replacement of hydrogen by an alkyl, acyl, or amino group. A derivative polynucleotide encodes a polypeptide which retains at least one biological function of the natural molecule. A derivative polypeptide is one modified, for instance by glycosylation or any other process, which retains at least one biological function of the polypeptide from which it was derived.

As used herein, the term "gene" or "recombinant gene" refers to a nucleic acid comprising an open reading frame encoding a biologically active agent, including exon and (optionally) intron sequences.

A particularly preferred pharmacologically active agent, i.e., a therapeutic or prophylactic agent, according to the invention is a nucleic acid.

The nucleic acid to be used in the instant invention can be any nucleic acid of interest, i.e., as explained above exhibiting a biological property. More particularly, the nucleic acid can be, as mentioned above, any nucleic acid encoding a natural, truncated, artificial, chimeric or recombinant product [e.g., a polypeptide of interest (including a protein or a peptide), a RNA, etc.] exhibiting a biological activity.

The nucleic acid is preferably a desoxyribonucleic acid (DNA) molecule (cDNA, gDNA, synthetic DNA, artificial DNA, recombinant DNA, etc.) or a ribonucleic acid (RNA) molecule (mRNA, tRNA, RNAi, RNAsi, catalytic RNA, antisens RNA, viral RNA, etc.). The nucleic acid may be single stranded or multiple stranded nucleic acid, preferably double-stranded nucleic acid or may be complexed. The nucleic acid may comprise hybrid sequences or synthetic or semi-synthetic sequences. It may be obtained by any technique known to persons skilled in the art, and especially by screening libraries, by chemical synthesis, or alternatively by mixed methods including chemical or enzymatic modification of sequences obtained by screening libraries.

In a particular embodiment, the therapeutic nucleic acid is of synthetic or biosynthetic origin, or extracted from a virus or from a unicellular or pluricellular eukaryotic or prokaryotic organism.

The therapeutic nucleic acid used in the present invention may be naked, may be complexed to any chemical, biochemical or biological agent, may be inserted in a vector, etc., when administered to the ciliary body tissue(s) or cells and/or to the extra-ocular muscle or cells.

As used herein, the term "naked DNA" refers to any nucleic acid molecule which is not combined to a synthetic, biosynthetic, chemical, biochemical or biological agent improving the delivery or transfer of said DNA, or facilitating its entry into the cell.

As used herein, the term "vector" refers to a nucleic acid molecule capable of transporting another nucleic acid to which it has been linked. This term also refers in the present application to any delivery carrier, such as a composition associated to a therapeutic or prophylactic nucleic acid in order to increase its cellular delivery.

Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form, are not bound to the chromosome. In the present invention, the plasmid is the most commonly used form of vector. The plasmid is a preferred form of naked DNA according to the invention.

Vectors may also be episomal DNA, yeast artificial chromosomes, minichromosomes or viral vectors wherein the viral vector is selected from the group consisting of a lentivirus, an adenovirus, an adeno-associated virus and a virus-like vector.

The vector may also be a lipid vesicle such as a liposome. Lipid based compounds which are not liposomes may further be used. For example, lipofectins and cytofectins are lipid-based positive ions that bind to negatively charged nucleic acid and form a complex that can ferry the DNA across a cell membrane. The invention is intended to include such other forms of expression vectors which serve equivalent functions and which become known in the art subsequently hereto.

In addition, the nucleic acid according to the invention may also contain one or more additional regions, for example regulatory elements of small or large size which are available to the skilled artisan such as a promoter region (constitutive, regulated, inducible, tissue-specific, etc.), for example sequences allowing and/or promoting expression in the ciliary body tissue(s) or cells and/or in the extra-ocular muscle or cells, a transcription termination signal, secretion sequences, an origin of replication and/or nuclear localization signal (nls) sequences which further enhance polynucleotide transfer to the cell nucleus. Such nls sequences have been described in the literature, including the SV40 large T antigen sequence [Dingwall and Laskey, Trends Biochem. Sci. 16 (1991) 478; Kalderon et al., Nature 311 (1984) 33].

Additionally, the nucleic acid may further comprise selectable markers useful in selecting, measuring, and monitoring nucleic acid transfer results (transfer to which tissues, duration of expression, etc.). The types of expression systems and reporter genes that can be used or adapted for use are well known in the art. For example, genes coding for a luciferase activity, an alkaline phosphatase activity, or a green fluorescent protein activity are commonly used. See Ausubel et al. [Current Protocols in Molecular Biology, John Wiley & Sons, N.Y. (1989), and supplements through May 1999].

The nucleic acid according to the invention may contain any nucleotide sequence of any size. The nucleic acid may thus vary in size from a simple oligonucleotide to a larger molecule such as a nucleotide sequence including exons and/or introns and/or regulatory elements of any sizes (small or large), a gene of any size, for example of large size, or a chromosome for instance, and may be a plasmid, an episome, a viral genome, a phage, a yeast artificial chromosome, a minichromosome, an antisense molecule, etc.

In a particularly preferred embodiment, the polynucleotide is a double-stranded, circular DNA, such as a plasmid, encoding a product with biological activity.

The nucleic acid can be prepared and produced according to conventional recombinant DNA techniques, such as amplification, culture in prokaryotic or eukaryotic host cells, purification, etc. The techniques of recombinant DNA technology are known to those of ordinary skill in the art. General methods for the cloning and expression of recombinant molecules are described in Maniatis et al. (Molecular Cloning, Cold Spring Harbor Laboratories, 1982), and in Ausubel et al. (Current Protocols in Molecular Biology, Wiley and Sons, 1987), which are incorporated by reference.

A preferred biologically active substance is an ocular active substance, i.e., a substance capable of exerting a beneficial effect on ocular cells. It may be a substance capable of compensating for a deficiency in or of reducing an excess of an endogenous substance. Alternatively, it may be a substance conferring new properties on the cells. It may be for example an antisense sequence or a polypeptide which can affect the function, morphology, activity and/or metabolism of ocular cells.

The down regulation of gene expression using antisense nucleic acids can be achieved at the translational or transcriptional level. Antisense nucleic acids of the invention are preferably nucleic acid fragments capable of specifically hybridizing with a nucleic acid encoding an endogenous ocular active substance or the corresponding messenger RNA. These antisense nucleic acids can be synthetic oligonucleotides, optionally modified to improve their stability and selectivity. They can also be DNA sequences whose expression in the cell produces RNA complementary to all or part of the mRNA encoding an endogenous ocular active substance. Antisense nucleic acids can be prepared by expression of all or part of a nucleic acid encoding an endogenous ocular active substance, in the opposite orientation. Any length of antisense sequence is suitable for practice of the invention so long as it is capable of down-regulating or blocking expression of the endogenous ocular active substance. Preferably, the antisense sequence is at least 20 nucleotides in length. The preparation and use of antisense nucleic acids, DNA encoding antisense RNAs and the use of oligo and genetic antisense is disclosed in WO92/15680, the content of which is incorporated herein by reference.

Among the biologically active polypeptides or proteins optionally expressed by a nucleic acid as described above or usable as a biologically active agent and suitable for practice of the invention are enzymes, blood derivatives, hormones, lymphokines, cytokines, chimiokines, anti-inflammatory factors, growth factors, trophic factors, neurotrophic factors, haematopoietic factors, angiogenic factors, anti-angiogenic factors, inhibitors of metalloproteinase, regulators of apoptosis, coagulation factors, receptors thereof, in particular soluble receptors, a peptide which is an agonist or antagonist of a receptor or of an adhesion protein, antigens, antibodies, fragments or derivatives thereof and other essential constituents of the cell.

Various retina-derived neurotrophic factors have the potential to rescue degenerating photoreceptor cells (Li and Turner, 1988a,b; Li et al., 1991; Anchan et al., 1991; Sheedlo et al., 1989, 1993; Guillemot and Cepko, 1992; Steele et al., 1993), and may be delivered trough a method according to the present invention.

Preferred biologically active agents may be selected from VEGF, Angiogenin, Angiopoietin-1, Del-1, acidic or basic Fibroblast Growth Factors (aFGF and bFGF), FGF-2, Follistatin, Granulocyte Colony-Stimulating factor (G-CSF), Hepatocyte Growth Factor (HGF), Scatter Factor (SF), Leptin, Midkine, Placental Growth Factor (PGF), Platelet-Derived Endothelial Cell Growth Factor (PD-ECGF), Platelet-Derived Growth Factor-BB (PDGF-BB), Pleiotrophin (PTN), Progranulin, Proliferin, Transforming Growth Factor-alpha (TGF-alpha), Transforming Growth Factor-beta (TGF-beta), Tumor Necrosis Factor-alpha (TNF-alpha), Vascular Endothelial Growth Factor (VEGF), Vascular Permeability Factor (VPF), CNTF, BDNF, GDNF, PEDF, NT3, BFGF, angiopoietin, ephrin, EPO, NGF, IGF, GMF, aFGF, NT5, Gax, a growth hormone, α-1-antitrypsin, calcitonin, leptin, an apolipoprotein, an enzyme for the biosynthesis of vitamins, hormones or neuromediators, chemokines, cytokines such as IL-1, IL-8, IL-10, IL-12, IL-13, a receptor thereof, an antibody blocking anyone of said receptors, TIMP such as TIMP-1, TIMP-2, TIMP-3, TIMP-4, angioarrestin, endostatin such as endostatin XVIII and endostatin XV, ATF, angiostatin, a fusion protein of endostatin and angiostatin, the C-terminal hemopexin domain of matrix metalloproteinase-2, the kringle 5 domain of human plasminogen, a fusion protein of endostatin and the kringle 5 domain of human plasminogen, the placental ribonuclease inhibitor, the plasminogen activator inhibitor, the Platelet Factor-4 (PF4), a prolactin fragment, the Proliferin-Related Protein (PRP), the antiangiogenic antithrombin III, the Cartilage-Derived Inhibitor (CDI), a CD59 complement fragment, vasculostatin, vasostatin (calreticulin fragment), thrombospondin, fibronectin, in particular fibronectin fragment gro-beta, an heparinase, human chorionic gonadotropin (hCG), interferon alpha/beta/gamma, interferon inducible protein (IP-10), the monokine-induced by interferon-gamma (Mig), the interferon-alpha inducible protein 10 (IP10), a fusion protein of Mig and IP10, soluble Fms-Like Tyrosine kinase 1 (FLT-1) receptor, Kinase insert Domain Receptor (KDR), regulators of apoptosis such as Bcl-2, Bad, Bak, Bax, Bik, Bcl-X short isoform and Gax, fragments or derivatives thereof and the like.

In a particularly preferred embodiment, the nucleic acid encodes a soluble fragment of the TNFα receptor, the TGFβ2 receptor, of VEGFR-1, VEGFR-2, VEGFR-3, CCR2 or MIP1.

The nucleic acid may also, in another preferred embodiment, encode an antibody, a variable fragment of a single-chain antibody (ScFv) or any other antibody fragment having recognition capacities for the purposes of immunotherapy.

In a particular embodiment of the present invention, the biologically active nucleic acid encodes a precursor of a therapeutic protein usable in the present invention such as those described above.

Furthermore, in another embodiment of the present invention, a mixture of nucleic acids encoding distinct biologically active products can be used. This variant allows co-expression of different products in the ocular cells.

Fundamental ways to deliver nucleic acids include in vivo gene transfer and ex vivo gene transfer. In vivo gene transfer involves introducing the nucleic acid specifically into the ciliary body tissue(s) or cells and/or into the extra-ocular muscle or cells of the patient using naked nucleic acid, complexed nucleic acid, nucleic acid vectors, etc., as described above. All two of the broad-based categories mentioned above may be used to achieve gene transfer in the context of the present invention. In ex vivo gene transfer according to the invention, any cells, in particular muscular cells, preferably smooth muscle cells, even more preferably cells from the ciliary body tissue(s) and/or from the extra-ocular muscle, are taken from the patient and grown in cell culture. The nucleic acid is transfected into said cells, and the transfected cells are preferably expanded in number and then reimplanted in the patient, preferably in the ciliary body tissue(s) or cells and/or in the extra-ocular muscle or cells. A particular cell usable in an ex vivo gene transfer according to the invention may be a fibroblast cell for example. Another biologically active product according to the present invention is thus a cell transfected with a nucleic acid of interest as described above or a cell expressing such a nucleic acid.

Pharmaceutical Compositions

In an embodiment, the present invention relates to the use of a biologically active agent, such as a therapeutic or prophylactic nucleic acid, for preparing a composition for the treatment or prevention of an ocular disease by administering said composition to the ciliary body tissue(s) or cells and/or to the extra-ocular muscle or cells of the subject to be treated, wherein the biologically active agent is present in a composition containing, in addition, a pharmaceutically acceptable excipient or diluent.

Another object of the invention relates to a pharmaceutical composition for preventing or treating an ocular disease, wherein said composition is intended for an administration into the ciliary body tissue(s) or cells and/or into the extra-ocular muscle or cells and comprises a biologically active agent as described above and preferably a pharmaceutically acceptable excipient or diluent.

The pharmaceutical preparation or composition according to the invention can consist essentially of the biologically active agent, preferably a naked nucleic acid, complexed nucleic acid, nucleic acid vector or delivery system, etc., in an acceptable carrier, excipient or diluent, or can comprise a slow release matrix in which the agent is embedded. Alternatively, where the complete nucleic acid delivery system can be produced intact from recombinant cells, e.g., plasmid vectors, the pharmaceutical preparation can comprise one or more cells, preferably ciliary body cells and/or extra-ocular muscle cells, which produce the secreted therapeutic protein.

Pharmaceutically compatible or physiologically acceptable carrier, excipient or diluent includes diluents and fillers which are pharmaceutically acceptable for methods of administration, are sterile, and may be selected from neutral to slightly acidic, isotonic, buffered saline (including phosphates, chloride, etc.), aqueous or oleaginous solutions or suspensions and more preferably from sucrose, trehalose, surfactants, proteins and amino acids. The pharmaceutically compatible or physiologically acceptable carrier, excipient or diluent is preferably formulated using suitable dispersing, wetting, suspending, soothing, isotonic or viscosity building agents, stabilizers, preservatives and appropriate buffer to form an isotonic solution. The particular pharmaceutically acceptable carrier and the ratio of active compound to carrier are determined by the solubility and chemical properties of the composition, the particular mode of administration, and standard pharmaceutical practice. Those skilled in the art will understand how to formulate such vehicles by known techniques.

An example of stabilizers is disodium edetate or the like. Examples of isotonic agents are glycerin, propylene glycol, polyethylene glycol, sodium chloride, potassium chloride, sorbitol and mannitol or the like. Examples of buffers are citric acid, sodium hydrogenphosphate, glacial acetic acid and trometamol or the like. Examples of pH adjusters are hydrochloric acid, citric acid, phosphoric acid, acetic acid, sodium hydroxide, sodium carbonate and sodium hydrogencarbonate or the like. An example of soothing agents is benzyl alcohol or the like. Examples of preservatives are benzalkonium chloride, benzethonium chloride, p-hydroxybenzoate esters, sodium benzoate and chlorobutanol or the like.

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxypropyl methylcellulose, hydroxyethyl cellulose, carboxymethyl cellulose, hydroxypropyl cellulose or other agents known to those skilled in the art. Such agents are typically employed at a level of from about 0.01 to about 2 wt. %.

Preparation forms of the pharmaceutical composition intended for administration to ciliary body tissue(s) or cells and/or to extra-ocular muscle or cells of the present invention are preferably liquid preparations.

The liquid preparations can be prepared, for example, by dissolving the biologically active agent in BSS (Balanced Salt Solution), a glycerin solution, a hyaluronic acid solution and the like. A particular composition comprises for example BBS (60%) and hyaluronic acid (40%). A stabilizer, an isotonic agent, a buffer, a pH adjustor, a soothing agent, a preservative, electrolytes, such as sodium, potassium, calcium, magnesium and/or chloride or the like can optionally be added in an adequate amount to the liquid preparations.

Methods for formulating and administering naked DNA to mammalian muscle tissue are disclosed in U.S. Pat. Nos. 5,580,859 and 5,589,466, the contents of which are incorporated herein by reference.

The pharmaceutical composition may comprise or the biologically active agent may be combined (in a use according to the present invention) with any additional active ingredient or adjuvant. The adjuvant may be selected from any substance, mixture, solute or composition facilitating or increasing the biological activity of the prophylactic or therapeutic agent such as any biologic, synthetic or biosynthetic agent which improves the delivery or transfer of said agent and may be assimilated to a vector (as delivery carrier) according to the invention. The adjuvant may be conditioned and administered separately or sequentially from the prophylactic or therapeutic agent containing composition and/or at a distinct site of injection. Treatment with multiple agents and/or adjuvants according to the invention need not be done using a mixture of agents and/or adjuvants but may be done using separate pharmaceutical preparations. The preparations need not be delivered at the same exact time, but may be coordinated to be delivered to a patient during the same period of treatment, i.e., within a week or a month or each other.

Any suitable therapeutic agents can be coordinated with the compositions of the present invention. Non-limiting examples of therapeutic agents which may be administered in addition to the above biologically active (prophylactic or therapeutic) agent(s) through a method according to the present invention also include permeabilizing agents such as a virus, a lipid vesicle, hyaluronic acid, lipid-based positive ions, polycationic emulsions, cationic peptides, polyplex, etc.; antibiotics and antimicrobial agents such as tetracycline hydrochloride, leucomycin, penicillin, penicillin derivatives, erythromycin, sulphathiazole and nitrofurazone; local anesthetics such as benzocaine; vasoconstrictors such as phenylephrine hydrochloride, tetrahydrozoline hydrochloride, naphazoline nitrate, oxymetazoline hydrochloride and tramazoline, hydrochloride; cardiotonics such as digitalis and digoxin; vasodilators such as nitro-glycerine and papaverine hydrochloride; antiseptics such as chlorhexidine hydrochloride, hexylresorcinol, dequaliniumchloride and ethacridine; enzymes such as lysozyme chloride and dextranase; hypotensives; sedatives; anti-tumor agents; steroidal anti-inflammatory agents such as hydro-cortisone, prednisone, fluticasone, prednisolone, triamcinolone, acetonide, dexamethasone, betamethasone, beclomethasone, and beclomethasone dipropionate; non-steroidal anti-inflammatory agents such as acetaminophen, aspirin, aminopyrine, phenylbutazone, mefanamic acid, ibuprofen, diclofenac sodium, indomethacin, colchicine, and probenocid; enzymatic anti-inflammatory agents such as chymotrypsin and bromelain seratiopeptidase; anti-histaminic agents such as diphenhydramine hydrochloride, chloropheniramine maleate and clemastine; anti-allergic agents; and analgesic compounds.

Actual dosage levels of active ingredients in the compositions of the present invention may be adapted so as to obtain an amount of active ingredient that is effective to obtain a desired biological activity.

It should be understood, however, that the specific dose level for any particular patient will depend upon a variety of factors including the body weight, general health, sex, diet, time, rates of absorption and excretion, combination with other drugs and the severity of the particular disease being treated.

The pharmaceutical compositions may conveniently be presented in unit dosage form and may be prepared by any of the methods well-known in the art of pharmacy. All methods include the step of bringing the active agent into association with a carrier as described above which constitutes one or more accessory ingredients. In general, the compositions are prepared by uniformly and intimately bringing the active agent into association with a carrier, preferably a liquid carrier.

Other delivery systems can include time-release, delayed release or sustained release delivery systems. Such systems can avoid, when required, repeated administrations of the active agent, increasing convenience to the subject and the physician. Many types of release delivery systems are available and known to those of ordinary skill in the art. They include polymer base systems such as poly (lactide-glycolide), copolyoxalates, polycaprolactones, polyesteramides, polyorthoesters, polyhydroxybutyric acid, and polyanhydrides. Delivery systems also include non-polymer systems that are: lipids including sterols such as cholesterol, cholesterol esters and fafty acids or neutral fats such as mono-di- and tri-glycerides; hydrogel release systems; sylastic systems; peptide based systems; wax coatings and the like.

Another embodiment of the present invention relates to the use of a biologically active agent as described above, preferably of a therapeutic nucleic acid, for preparing a pharmaceutical composition as described above for the prevention or treatment of an ocular disease in a subject by administering said composition to the ciliary body tissue(s) or cells and/or to the extra-ocular muscle tissue or cells of the subject to be treated.

Treatment

The present invention provides an in vivo method for delivering a biologically or pharmacologically active agent as described previously, especially a therapeutic or prophylactic nucleic acid, or a composition according to the invention, to the ocular sphere of a subject, in particular to the inner or posterior part of the eye, comprising administration of said agent or composition into the ciliary body tissue(s) or cells and/or into the extra-ocular muscle tissue or cells.

A further object of the invention is a method of producing a therapeutic or prophylactic protein in a subject ocular tissue (s) or cells comprising administering a nucleic acid encoding said protein into the ciliary body tissue(s) or cells and/or to the extra-ocular muscle tissue or cells, wherein said nucleic acid is delivered to said ocular tissue(s) or cells and expressed as explained above.

An object of the invention also relates to a method of protecting a subject against an ocular disease or impairment of the eye comprising administering a biologically or pharmacologically active agent as described previously, preferably a nucleic acid, or a composition according to the invention, to the ciliary body tissue(s) or cells and/or to the extra-ocular muscle tissue or cells, wherein said agent or composition is delivered to ocular tissue(s) or cells and protects against the ocular disease.

Still another aspect of the invention is a method of treating an ocular disease or an impairment of the eye affecting a subject comprising administering to the subject a biologically or pharmacologically active agent as described previously, preferably a nucleic acid encoding a therapeutic substance, or a composition according to the invention, to the ciliary body (muscle or epithelium) and/or the extra-ocular muscle, wherein said agent or composition is delivered to impaired ocular tissue(s) or cells.

Another aspect of the invention relates to gene therapy. This kind of therapy consists in the introduction of nucleic acid into a cell or tissue either in vivo or ex vivo. In some instances, the nucleic acid is intended to replace (or act in place of) or to correct a functionally deficient endogenous gene, to confer on the host the ability to produce a therapeutic polypeptide, to cause repression of an undesirable gene product, or to stimulate an immune response.

In a particular aspect, the present invention is directed to a method to treat a disease comprising the administration of a nucleic acid, preferably a chimeric oligonucleotide as defined above, capable of reverting or inducing a mutation in a target gene of target cells, gene expression of which is associated to that disease, in a subject host in need of such treatment, wherein the method used for delivering in vivo said nucleic acid into said target cells is the method for delivering in vivo nucleic acid according to the present invention.

In a particular embodiment, the method for delivering in vivo a nucleic acid into ocular cells according to the present invention is used to treat or to prevent a genetic ocular disease due to the presence of at least a mutation in a gene of ocular cells, mutated gene whose expression is responsible for said ocular disease. In this method, said nucleic acid is complementary to a genomic DNA fragment sequence of the target mutated gene of said cells with the exception of the mutation which is desired to be reverted in said target mutated gene.

In another preferred embodiment, the method for delivering in vivo a nucleic acid into ocular cells according to the present invention is used to voluntary induce a mutation in a gene of that ocular cells of an animal, mutated gene whose expression is responsible for an ocular disease, in order to obtain an animal or human tissue or organism which can serve as a model for studying said ocular disease or for screening compounds capable of treating that ocular disease.

Subjects who may beneficiate of the above described therapeutic or prophylactic methods may be any animal, in particular any mammalian, preferably a human that suffers or can suffer from any eye disease or eye condition requiring treatment with any ocular drug, protein, or peptide.

The invention thus relates to the use of such a method to prevent or treat various ocular diseases or impairments of the eyes, including but not limited to ocular inflammatory diseases, ischemic diseases, proliferative diseases (for example a neovascular or a glial disease), neurodegenerative diseases and glaucoma, either alone or in combination with additional treatments.

Examples of Ocular Diseases Treatable using the Present Invention

Non-limiting examples of ocular diseases and disorders that may be treated by various embodiments of the present invention include ocular proliferative diseases, ocular neurodegenerative diseases, glaucoma, ocular infectious diseases, ocular inflammatory diseases (such as conjunctivitis, keratitis, endothelitis, uveitis, choroiditis, retinitis, retinochoroiditis, anterior uveitis, and inflammatory optic neuropathies), retinal degenerations (in particular retinitis pigmentosa, peripheral retinal degeneration, macular degeneration such as dry age-related macular degeneration), ischemic retinopathy (in particular retinopathy of prematurity and diabetic retinopathy), retinal vascular diseases, ocular ischemia syndrome and other vascular anomalies, choroidal disorders and tumors, vitreous disorders, glial proliferation such as proliferative vitreo retinopathy and glial proliferation associated to diabetic pre retinal engiogenesis, etc.

Major diseases that may be prevented or treated by the present invention are described below:

Intraocular inflammation regroup all types of inflammation of the intraocular tissues, mainly uvea and retina. Intraocular inflammations may be from immunologic causes, infectious causes, iatrogenic causes or of unknown etiologies. They may be acute, recurrent or chronic. Intraocular inflammations are among the most causes of curable blindness. Posterior segment intraocular inflammations may be associated to vasculitis, optic neuritis, vitritis and chorea retinitis.

Inherited retinal dystrophies or retinitis pigmentosa are inherited blinding diseases due to mutations or deletions in gene implicated in the visual cycle. They begin in the young age and progress slowly until total blindness. Loss of photoreceptors is associated to loss of retinal pigment cells and to vascular and optic nerve atrophy at the later stages. Some of these inherited degeneration are due to mutation in mitochondrial DNA.

There are two major types of glaucoma: chronic glaucoma or primary open-angle glaucoma (POAG) and acute closed-angle glaucoma. Other variations include congenital glaucoma, pigmentary glaucoma, neovascular glaucoma and secondary glaucoma. Glaucoma is similar to ocular hypertension but with accompanying optic nerve damage and vision loss. Glaucoma is usually treated with eye drops, laser, or conventional eye surgery. If not treated, glaucoma will cause blindness.

Angiogenesis is the formation of new capillary blood vessels leading to neovascularization. Angiogenesis is a complex process which includes a series of sequential steps including endothelial cell mediated degradation of vascular basement membrane and interstitial matrices, migration of endothelial cells, proliferation of endothelial cells, and formation of capillary loops by endothelial cells. Though angiogenesis is a normal process for the development or maintenance of the vasculature, pathological conditions (i.e., angiogenesis dependent diseases) arise where blood vessel growth is actually harmful. Angiogenesis is notably associated with important diseases of ocular tissue, including diabetic retinopathies, age related macular degeneration, retinopathy of prematurity, corneal graft rejection, neovascular glaucoma and corneal scaring. Any abnormal growth of blood vessels in the eye can scatter and block the incident light prior to reaching the retina. Neovascularization can occur at almost any site in the eye and significantly alter ocular tissue function. Some of the most threatening ocular neovascular diseases are those which involve the retina. For example, many diabetic patients develop a retinopathy which is characterized by the formation of leaky, new blood vessels on the anterior surface of the retina and in the vitreous causing proliferative vitreoretinopathy. A subset of patients with age related macular degeneration develop subretinal neovascularization which leads to their eventual blindness.

Diabetic Retinopathy occurs when the retinal vessels inside the eye leak blood and fluids into the surrounding tissue. About 80% of patient with diabetes develop diabetic retinopathy. This disease is generally treated using a laser. However, laser therapy involves complications including retinal vein occlusion, loss of visual acuity, vitreous hemorrhage and sometimes fails. If left untreated, diabetic retinopathy may cause blindness.

Retinopathy of Prematurity (ROP) affects prematurely born babies. It consists of the abnormal growth of blood vessels within the retinal and vitreous. Progression to later stages of ROP can lead to the formation of scar tissue on the retina, vitreous hemorrhage, and retinal detachment. The treatment is usually performed either by laser or cryotherapy (freezing).

Ischemic retinopathies are retinopathies associated to vascular occlusion (capillaries or large vessels) that lead to neuroretinal suffering, cell death and neo angiogenesis.

Macular degeneration is a disease that affects central vision and leads to loss of vision. Although there are forms of macular degeneration that strike young people, the condition occurs most commonly in people who are over 60 years of age. This disorder is thus called age-related macular degeneration (AMD). Because only the center of a person's vision is usually affected, blindness rarely occurs from the disease. However, injury to the macula in the center of the retina can destroy the ability to see straight ahead clearly. Dry forms associate degeneration of neuroretina, RPE cells and choroids. Wet forms associate previously described phenomenons and growth of neovessels from the choriocapillaries and/or retinal vessels, sub retinal detachment and hemorrhages, sub epithelial hemorrhages and tears, etc. Macular degeneration usually occurs after the age of sixty. While your central vision is reduced, most patients retain some vision and never go totally blind.

Keratitis is an inflammation of the cornea. Keratitis can be caused by bacterial, viral, or fungal infections, dry eyes resulting from disorders of the eyelid or diminished ability to form tears, exposure to very bright light, foreign objects that injure or become lodged in the eye, sensitivity or allergic reactions to eye makeup, dust, pollen, pollution, or other irritants and vitamin A deficiency.

Macular pucker (also called epiretinal membrane, retinal wrinkling, premacular fibrosis, and cellophane maculopathy) is due most often to age-related shrinkage of the vitreous which pulls away from the retina, causing the retina to scar and wrinkle. Other causes of macular pucker include trauma (from surgery or an eye injury), retinal detachment, inflammation, and problems with the retinal blood vessels. The only treatment is surgery which consists of a vitrectomy (removal of the vitreous) combined with peeling away of the scar tissue. The most common complication of vitrectomy is an increase in the rate of cataract development.

The treated eye disease may be chosen from scleritis, conjunctivitis, keratitis, endothelitis, uveitis, chorofditis, retinitis, retinochoroiditis, anterior uveitis, retinopathy of prematurity, diabetic retinopathy, proliferative vitreo retinopathy, inherited retinal dystrophies, age-related macular degeneration, open angle glaucoma, neovascular glaucoma, ischemic retinopathy, etc.

A preferred aspect of the invention is a method of treating chronic uveitis comprising administering to the ciliary body tissue(s) or cells and/or to the extra-ocular muscle tissue or cells of a mammal suffering therefrom a nucleic acid encoding a soluble receptor for TNF alpha.

Another preferred aspect of the invention is a method of treating intraocular neovessels or macular oedema comprising administering to the ciliary body tissue(s) or cells and/or to the extra-ocular muscle tissue or cells of a mammal suffering therefrom a nucleic acid encoding an anti VEGF, an anti VEGF receptor or an anti PLGF.

A further preferred aspect of the invention is a method of treating or delaying retinitis pigmentosa comprising administering to the ciliary body tissue(s) or cells and/or to the extra-ocular muscle tissue or cells of a mammal suffering therefrom a nucleic acid encoding a neurotrophic factor as described above.

Another preferred aspect of the invention is a method of treating diabetic retinopathy comprising administering to the ciliary body tissue(s) or cells and/or to the extra-ocular muscle tissue or cells of a mammal suffering therefrom a nucleic acid encoding an anti IRS-1 or IGF-1.

In methods and uses according to the invention, the ciliary body tissue(s) or cells and/or to the extra-ocular muscle tissue or cells may be subjected to a treatment to improve nucleic acid transfer before, during or after said transfer. This treatment may be of pharmacological nature and in the form of a local or systemic application, or may be an enzymatic, permeabilizing, surgical, mechanical, thermal or physical treatment such as those described before.

Kits

In accordance with the methods of the present invention, kits for preventing or treating an ocular disease are envisioned.

Devices and composition according to the present invention may be supplied together in a kit. Within the kit, the components may be separately packaged or contained. Other components such as excipients, carriers, other drugs or adjuvants, instructions for administration of the active substance or composition, and administration or injection devices can be supplied in the kit as well. Instructions can be in a written, video, or audio form, can be contained on paper, an electronic medium, or even as a reference to another source, such as a website or reference manual.

In particular, the invention includes a kit containing dried lyophilized plasmid, the dilution medium for said plasmid, and a single used electrode device as described above.

Other aspects and advantages of the present invention will be described in the following examples, which should be regarded as illustrative and not limiting the scope of the present application.

Experimental Part

In the present invention, inventors have designed a novel electrotransfer technique to specifically transfect notably ocular ciliary muscles. Plasmid encoding for either green fluorescent protein (GFP) or luciferase (luc) have been used to trace and dose post-transfection gene expression. The therapeutic potential of this technique is evaluated in rats with endotoxin-induced uveitis (EIU) using a gene encoding for human TNF-α soluble receptors I (hTNFR-Is).

Material and Methods

Animals:

Female Lewis rats, 6-7 weeks old weighing 150-200 g (IFFA CREDO, Lyon, France) were used. Experiments were conducted in accordance with the ARVO Statement for the Use of Animals in Ophthalmic and Vision Research. Rats were held for 1 week before inclusion in the study. For experiments, rats were anesthetized by intraperitoneal pentobarbital injection (40 mg/kg). At the end of the experiments, rats were sacrificed by an overdose of pentobarbital.

Plasmids:

pVAX2 consists in a pVAX1 plasmid (Invitrogen) in which the promoter was replaced by the pCMVβ plasmid promoter. The pCMVβ (Clontech) was digested with EcoRI, then blunt ended by the Klenow fragment, and finally digested by BamHI. A resulting 629 bp fragment corresponding to the CMV promoter was purified after agarose gel electrophoresis. This promoter was ligated into a HincII-BamHI pVAX1 fragment to give pVAX2.

pVAX2-luc is a 4.6 kb plasmid vector encoding a cytosolic firefly luciferase plus protein under the control of the CMV promoter.

Plasmid pEGFP-C1 is a 4.7 kb plasmid carrying the Green Fluorescent Protein gene under control of a CMV promoter (Clontech, Palo Alto, Calif.).

Plasmid pVAX2 hTNFR-Is/mIgG1 is a 4.3 kb plasmid encoding a chimeric protein of human TNF-α soluble receptor type I (hTNFR-Is) linked to the Fc portion of immunoglobulin G1 (IgG1) cloned into a pVAX2 backbone. This chimeric protein has a longer half-life compared to the natural monomeric equivalent hTNFR-Is.

Electrotransfer to Rat Ciliary Muscle

For electrotransfer experiments, the eye is exposed and held in position using a surgical sheet. Intramuscular injection into the ciliary muscle was performed in the temporal superior quadrant using a 30G needle on a 100 µl micro fine syringe (Hamilton, Spain). To reach the ciliary muscle located below the sclera posterior to the limbus, the intra ciliary muscle injection was carried out through a tunneled corneal incision. When the needle had crossed the limbus, it was inserted slightly deeper for a distance of 1 mm and the plasmids (diluted in 10 µl of 1× saline) were injected. Post injection, a small sub scleral bleb is formed (FIG. 1A).

Figure 1B:
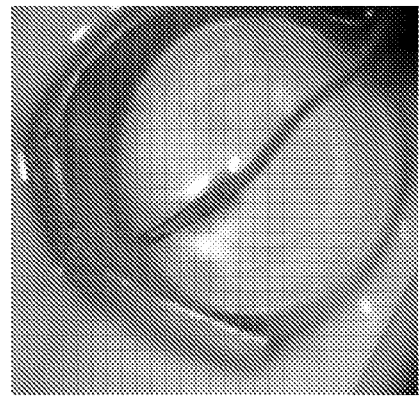

For electrotransfer, a specially designed sharp iridium/platine electrode (500 µm in diameter), naked on 2 mm and then covered with silicone on the rest of its length, was inserted through the corneal tunnel and connected to the cathode. The anode return electrode consisted of a platine 0.3 mm thick sheet, 5 mm length and 2.5 mm wide, designed to exactly fit the rat scieral surface overlying the ciliary body (FIGS. 1B and 1b).

Figure 1C:
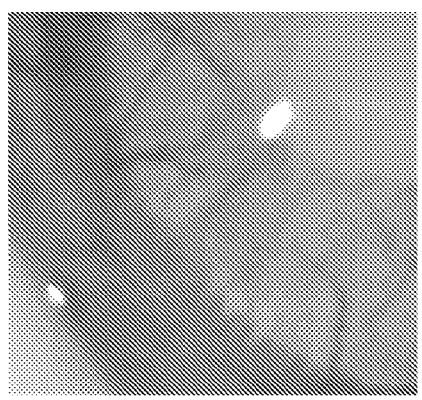
Figure 1D:
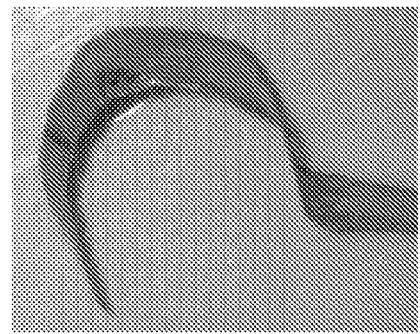

Electrotransfer generator was set to deliver an electric field intensity of 200 Volts/cm. Eight consecutive pulses (180 ms between pulses) of 10 Volts and 20 ms duration each were delivered using the above system. This electric field intensity did not cause any clinically detectable structure damage or tissue burns (FIG. 1C).

Experimental Design:

pVAX2-luc or pEGFP-C1 plasmids were used to locate and dose the proof of concept for expression of reporter genes in the ciliary muscle:

1. Three µg of pEGFP-C1 plasmid in 10 µl of saline, were injected in the ciliary muscle of 12 eyes (12 rats). In 4 eyes (4 rats), no additional treatment was performed. In 8 eyes (8 rats), electrotransfer was performed immediately after the injection as previously described.

Four additional rats (4 eyes) were used as controls and received 10 µl of saline in the ciliary muscle of the right eye. In two of these rats (2 eyes), the saline injection was followed by electrotransfer. All animals were examined at day 1 and 8 and sacrificed at day 8 by an overdose of pentobarbital. The treated eyes were enucleated and snap frozen. Cryo sections (8 µm thick) were prepared for routine histology and immunohistochemistry staining.

2. Three µg of pVAX2-luc in 10 µl of saline were injected in the ciliary muscle of both eyes of 24 rats. Injection of the plasmid was followed by electro-transfer in the left eyes of these 24 rats. On days 6, 12, 22 and 30 after treatment, six of the rats were sacrificed. At each time point, the eyes were dissected, the entire ciliary muscle removed and snap frozen at −80° C. and used for evaluation of luciferase (luc) activity. Four eyes of two additional untreated rats were used as negative control for luc expression.

GFP Histochemistry and α-Smooth Muscle Actin Immunohistochemistry

At day 8 after electrotransfer of pEGFP-C1, the eyes were enucleated, fixed in 4% paraformaldehyde for 1 hour, rinsed in 1×PBS, embedded in OCT compound and cryo-sectioned (8 µm). For 3 eyes treated with electrotransfer of pEGFP-C1, and 2 eyes simply injected with pEGFP-C1, transversal 8 µm sections of the eyes were performed in order to obtain transversal sections of the circular myofibres of the ciliary muscle. For the other eyes, sagital 8 µm sections were performed (parallel to the optic axis). To visualize the cell nuclei, sections were stained 5 min with 4',6-diamino-2-phenylindole (DAPI) solution diluted 1/3000 (Sigma-Aldrich, St-Quentin Fallavier, France), washed again in PBS and mounted in glycerol/PBS (1/1). Sections were examined under a fluorescence microscope (Leica, Switzerland) and numeric microphotographs were taken with a constant exposure time for all sections.

Immunofluorescent staining with mouse anti-human alpha-smooth muscle actin (anti-α-sm-1) monoclonal antibody (Chemicon, Temecula, Calif.) was performed to localize the ciliary muscle on transversal and frontal sections. Tissue sections were fixed for 5 min in acetone at −20° C. and air-dried. Dilution of supernatants was done in PBS containing 3 mM EGTA. Anti-α-sm-1 was used at a concentration of 5 µg/ml. As second antibodies, inventors used Texas Red® dye conjugated AffiniPure donkey anti-mouse IgG (Jackson Immunoresearch, West Grove, Pa.) diluted 1:50. Nuclei were stained by incubation 5 min with 4',6-diamino-2-phenylindole (DAPI) solution diluted 1/3000 (Sigma-Aldrich, St-Quentin Fallavier, France). Sections were washed again in PBS and mounted in glycerol/PBS (1/1). Rat pre-immune serum instead of the primary antibody was used as a negative control.

In Vitro Measurement of Luciferase Activity:

Rats receiving ciliary injection of 3 µg pVAX2-luc in the right eye and injection followed by electrotransfer in the left eyes were sacrificed on day 6, 12, 22 and 30 after treatment. The eyes were enucleated and dissected under an operating microscope, the ciliary body and muscle and the iris complex removed, snap frozen in liquid nitrogen and kept at −80° C. until tested. Each sample was then homogenized in 0.3 ml of cell culture lysis reagent (Promega, Charbonniere, France) supplemented with protease inhibitor cocktail (Boehringer, Mannheim, Germany) (one tablet for 50 ml). After centrifugation 10 min at 15000 g and 4° C., the luciferase activity was assessed on 10 µl of the supernatants placed in a white 96 wells plate. The detector was a Wallac Victor luminometer (EG&G Wallac, Evry, France) which adds 50 µl of luciferase assay substrate (Promega) to the sample and integrates the light produced by the sample during 10 s. Results are given for the whole sample in counts per second (cps).

Effect of hTNFR-Is/mIgG1 Plasmid Electro-Transfer:

The production of hTNFR-Is in the aqueous humor and in the serum was evaluated on the 7$^{th}$ day after pVAX2 hTNFR-Is/mIgG1 injection to the ciliary muscle with (or without) additional electro-transfer. To optimize the experimental conditions for sampling in the aqueous humor, 30 µg of pVAX2 hTNFR-Is/mIgG1 (in 10 µl saline) were injected in the right eye of 16 rats, followed by electro-transfer in 8 right eyes of these 16 rats. On day 6 after treatment, the rats were sacrificed. The serum of these 16 rats was sampled. The aqueous humors from right and left eyes was obtained and evaluated separately for each eye. Aqueous humors from the 16 left (contra lateral, not treated) eyes were used as control of hTNFR-Is levels.

The biological effect of the hTNFR-Is produced within the eye after injection of pVAX2hTNFR-Is/mIgG1 in the ciliary muscle (with or without additional electro-transfer) was evaluated in rats with Endotoxin-Induced Uveitis (EIU), a model for acute human intraocular inflammation (2-5).

Twenty four rats received an injection of 3 µg of pVAX2hTNFR-Is/mIgG1 in both eyes. The plasmid injection was followed by electrotransfer in 12 of these 24 rats. Twelve control rats received an injection of 10 µl saline in the ciliary muscle of both eyes followed by electro transfer. Eight additional rats received an injection of the "empty" plasmid pVAX2 (without the gene encoding hTNFR-Is) in the ciliary muscle. The empty plasmid injection was followed by electro-transfer in the right eyes of these 8 rats.

Seven days after the above treatments, EIU was induced in all 44 rats by injection of 150 µg of Salmonella Typhimurium LPS (Sigma Aldrich) in the right hind footpad.

Clinical scores of EIU were recorded at 24 hours after the LPS challenge and the rats were sacrificed.

In each group of rats, aqueous humors obtained from eight eyes were used to evaluate the level of secreted rat TNF-α. To allow accurate evaluations, two aqueous humors from two eyes receiving the same treatment and demonstrating similar clinical score of EIU were pooled. Four eyes of each group (except the group of rats treated with empty plasmid) were cryo sectioned and processed for histology scoring of infiltrating inflammatory cells.

TABLE 1

Summary of all experimental animal groups

| Number of rats | Treatment | ET | EIU | Fate |
|---|---|---|---|---|
| 4 | pEGFP-C1, 3 µg | | 0 | Cryosection day 8 |
| 8 | pEGFP-C1, 3 µg | + | 0 | Cryosection day 8 |
| 2 | Saline, 10 µl | | 0 | Cryosection day 8 |
| 2 | Saline, 10 µl | + | 0 | Cryosection day 8 |
| 24 | pVAX2-luc 3 µg OD pVAX2-luc 3 µg OS | + | 0 | Luciferase activity kinetics |
| 2 | None (OD and OS) | 0 | 0 | |
| 8 | pVAX2 hTNFR-Is/mIgG1 30 µg | | 0 | Sampling hTNFR-Is |
| 8 | pVAX2 hTNFR-Is/mIgG1 30 µg | + | 0 | Sampling hTNFR-Is |
| 12 | None | | + | 8 for hTNFR-Is sampling in AH 4 for histology grading of EIU |
| 12 | pVAX2 hTNFR-Is/mIgG1 3 µg | | + | 8 for TNF-α sampling in AH 4 for histology grading of EIU |
| 12 | pVAX2 hTNFR-Is/mIgG1 3 µg | + | + | 8 for TNF-α sampling in AH 4 for histology grading of EIU |
| 12 | Saline 10 µl | + | + | 8 for TNF-α sampling in AH 4 for histology grading of EIU |
| 12 | 0 | | + | 8 for TNF-α sampling in AH 4 for histology grading of EIU |
| 8 | Empty plasmid 3 µg | + | + | 8 for TNF-α sampling in AH |

Evaluation of pVAX2 hTNFR-Is/mIgG1 Electrotransfer on the Intensity of EIU

The clinical grading system as published previously (5) was used with slight adaptations. Briefly, grade (0) indicates no inflammation. Grade (1) indicates slight vasodilation of iris and conjunctival vessels without flare or cells in the anterior chamber (AC). Grade (2) indicates the presence of moderate vasodilation of iris and conjunctival but without evident flare or cells in the AC. Grade (3) indicates the presence of intense iris vessels vasodilation with flare and less than 10 cells per slit lamp field in the AC. Grade (4) indicates the presence of clinical signs similar to grade 3 with many cells in the AC forming a hypopion or fibrin. Grade (5) indicates the presence of intense inflammatory reaction in the AC with total seclusion of the pupil.

For histology evaluation of EIU intensity, 4 eyes of each groups were enucleated, fixed in 4% paraformaldehyde for 1 hour, rinsed in PBS, mounted in OCT and whole globes cryo sectioned. The globe sections through the optic nerve of each eye to be evaluated were stained with hematoxylin-eosin. The mean number of infiltrating cells per section present in the anterior and posterior segments was obtained by dividing the total number of cells by the number of slides examined for the same eye. The number of infiltrating cells was recorded by an investigator unaware of the treatment.

Soluble hTNFR-Is Level in Aqueous Humor of Rats with or without EIU

Levels of hTNFR-Is receptors were measured by ELISA using a human receptor type I specific kit (Duoset, R&D Systems, Abingdon, UK), according to the manufacturer's instructions. In order to evaluate the systemic passage of hTNFR-Is produced in the anterior segment of the eyes, serum concentrations of hTNFR-Is were determined by the same method.

TNF-α Level in the Aqueous Humor of Rats with or without EIU

The obtained aqueous humors were immediately centrifuged and the cell free fraction collected and frozen at −20° C. before analysis. Levels of rat TNF-α were measured using a specific ELISA for rat TNF-α (Duoset, R&D Systems, Abingdon, UK). The same procedure as for the evaluation of TNF-α receptors levels was used, with a capture antibody at 4 µg/ml, a detection antibody at 100 ng/ml, and a two-fold serial dilution of the recombinant rat TNF-α from 400 pg/ml to 62.5 pg/ml.

Statistical Analysis

Results are expressed as means±standard error of the mean (SEM). Data were compared using ANOVA with pair wise comparisons by the Bonferroni/Dunn method.

Results

Safety of Electrotransfer (also Referred as Electroporation)

Clinical examination of treated eyes at the slit lamp on day 1 and 8 after GFP or saline electrotransfer disclosed no clinical sign of intraocular inflammation or gross structural damage.

After sacrifice of the rats, histology sections of the treated eyes were obtained and examined. Histology study of the sections through the needle insertion for intra ciliary muscle injection and electro-transfer sites demonstrated in a few cases, the presence of a mild cell infiltrate in the cornea tunnel but not in the ciliary muscle. Ocular structures were unaffected with normal anatomy preserved.

Also, aqueous humor TNF-α in rat eyes with EIU undergoing electro transfer after injection of saline solution was not increased when compared to aqueous humor TNF-α in control EIU rats (P=0.10). Thus, electrotransfer per se, does not enhance TNF-α production in eyes of rats with EIU.

Electrotransfer of Plasmids Encoding for GFP in the Ciliary Muscle

Figure 2D:
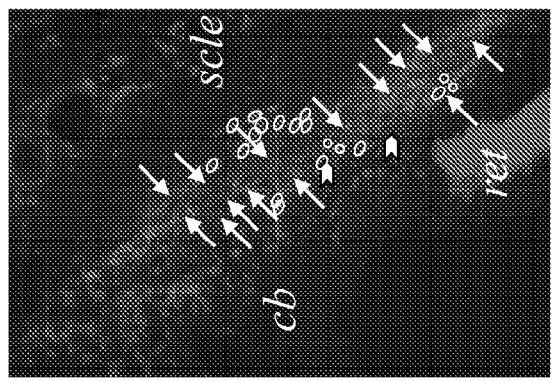
Figure 2C:
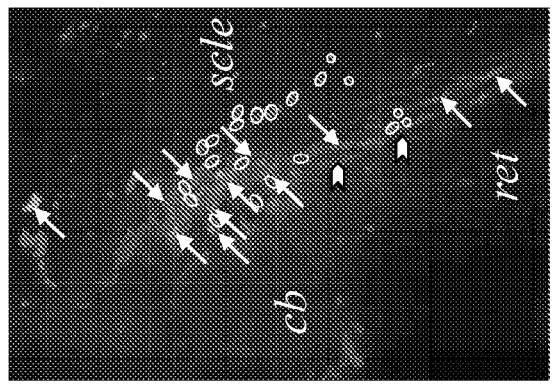
Figure 2B:
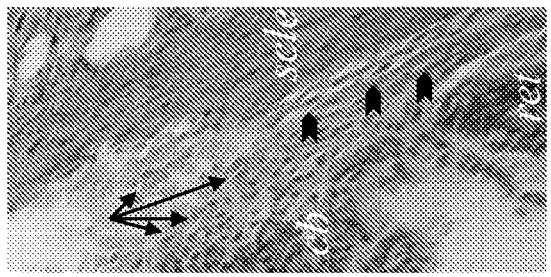
Figure 2A:

Eight days after electro transfer of GFP encoding plasmid, longitudinal sections demonstrate a specific fluorescent signal localized in the ciliary muscle. Elongated fluorescent cells correspond to transversal myofibres of the ciliary muscle (FIGS. 2A, a and B) as demonstrated by immunolocalization of alpha smooth muscle actin (α-sm-1) (FIG. 2C).

Figure 3C:
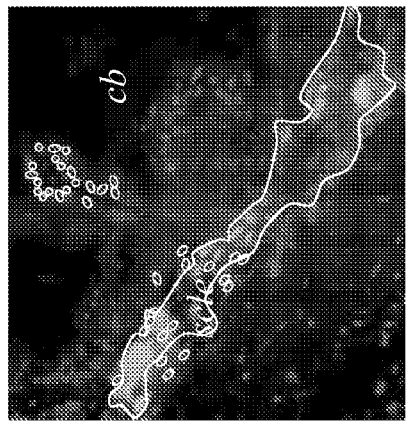
Figure 3B:
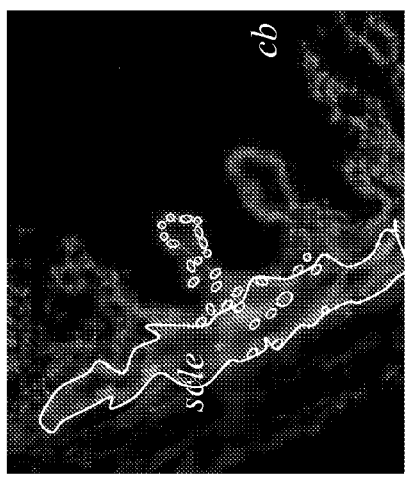
Figure 3A:
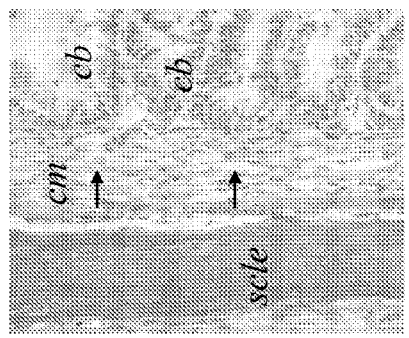
Figure 3E:
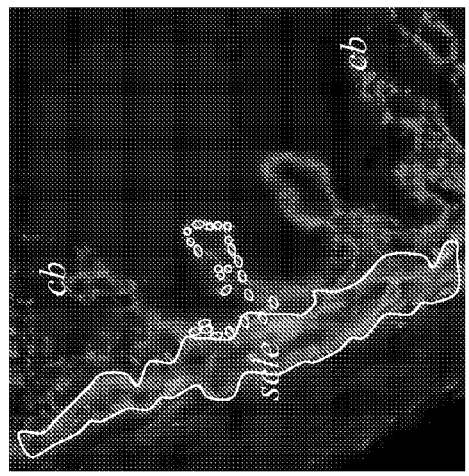
Figure 3D:
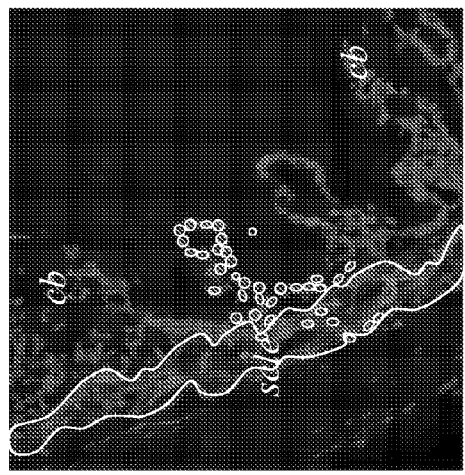

On anterior frontal sections, circular myofibres are identified surrounding the ciliary body just below the sclera (FIG. 3A). GFP is highly expressed on both anterior sections, showing circular fibres (FIG. 3B) and on more posterior sections, showing GFP staining in round tubes corresponding to radial and longitudinal fibres (FIG. 3C). On anterior frontal sections, the circular fibres of the ciliary muscles are well identified by α-sm-1 immunostaining (FIG. 3D). The co-localization of GFP and α-sm-1 confirmed that GFP was expressed in muscle fibres after electrotransfer (FIG. 3E).

When GFP plasmid injection was performed without electro-transfer, sparse round fluorescent dots were observed at the root of the ciliary body, but the circular myofibres did not show any fluorescent signal (FIG. 4A, a).

Kinetics of Luciferase Expression

No significant luciferase activity was measured in the ciliary muscle of rats injected with 3 µg of pVAX2-luc without electrotransfer. However, high and sustained luciferase activity was measured in the ciliary muscle of rats receiving electrotransfer after injection of 3 µg pVAX2-luc until at least 30 days, at a time when a stable value seemed to be reached (FIG. 5).

Production of Soluble Receptor hTNFR-Is in the Aqueous Humor

In the aqueous humor of rat eyes without EIU, 7 days after injection of 30 μg pVAX2 hTNFR-Is/mIgG1 (without electrotransfer), the mean level of hTNFR-Is was 274±39 μg/ml (n=4).

In eyes treated with a combination of electrotransfer, the mean level was 691±121 pg/ml (n=4) (P<0.01). In the contra lateral eyes of rats receiving the plasmid injection in the fellow eye with or without electrotransfer, no detectable level of hTNFR-Is was found. In the serum of rats from all groups, hTNFR-Is levels were below detection, thus demonstrating the advantage of the invention to allow local transgenic protein production and delivery.

In rats with EIU, the mean hTNFR-Is level was 181±108 pg/ml (n=8) in the group of rats after ciliary injection of 30 μg of pVAX2 hTNFR-Is/mIgG1 only. In aqueous humor of eyes receiving the combination of injection with electro-transfer, the level of hTNFR-Is was significantly higher 1070±218 pg/ml (n=8), P<0.005. In rats with EIU not receiving the intra ciliary plasmid injection, with or without electro-transfer (control groups), no detectable levels of hTNFR-Is was found demonstrating that the ELISA test was specific for human TNFR-Is and did not interfere with rat soluble TNF receptors.

In the serum of rats with EIU, hTNFR-Is levels were below detection whether eye treatment was carried out with plasmid alone or with the combination of electro-transfer, demonstrating that systemic diffusion of intraocular hTNFR-Is was negligible.

Effect on Clinical EIU

When the low hTNFR-Is/mIgG1 plasmid dose of 3 μg was used for intra ciliary muscle injection, the mean EIU score was 3.7±0.2, similar to EIU scores of 3.8±0.2 and 3.9±0.1 (P=0.81 and P=0.62 respectively) for the EIU, non plasmid injected group of rats and those injected with saline electrotransfer (FIG. 7A). The mean clinical EIU score was significantly reduced in the group of rats who were electrotransferred with 3 μg of pVAX2 hTNFR-Is/mIgG1 (1.2±0.2, P<0.0001), demonstrating that the combination with electrotransfer significantly reduced clinical uveitis when compared to the simple plasmid injection (P<0.0001) or to no treatment (P<0.0001).

In the group of rats treated with intra ciliary injection of 3 μg empty plasmid combined with electrotransfer the EIU score was 3.8±0.2. The EIU score in this group of rats was not significantly different from that obtained in the plasmid-injected EIU control group (P=0.91) or those EIU rats receiving saline electrotransfer (P=0.85).

Effect on Cellular Infiltrate

In the control group of rats with EIU, the mean number of infiltrating cells in the anterior segment was 316±14 (n=4) and 272±66 in the posterior segment. No significant difference in the number of infiltrating cells in the anterior (369±65, P=0.77) or in the posterior segment (261±32, p=0.99) was observed in the group of rats treated with injection of 3 μg of pVAX2 hTNFR-Is/mIgG1 only. Intra ciliary injection of the empty plasmid combined with electrotransfer had no effect on the number of infiltrating cells in the anterior segment (322±26, p=0.99) or in the posterior segment (255±13, p=0.98) when compared to the control, non-plasmid-injected EIU group.

Figure 8A:
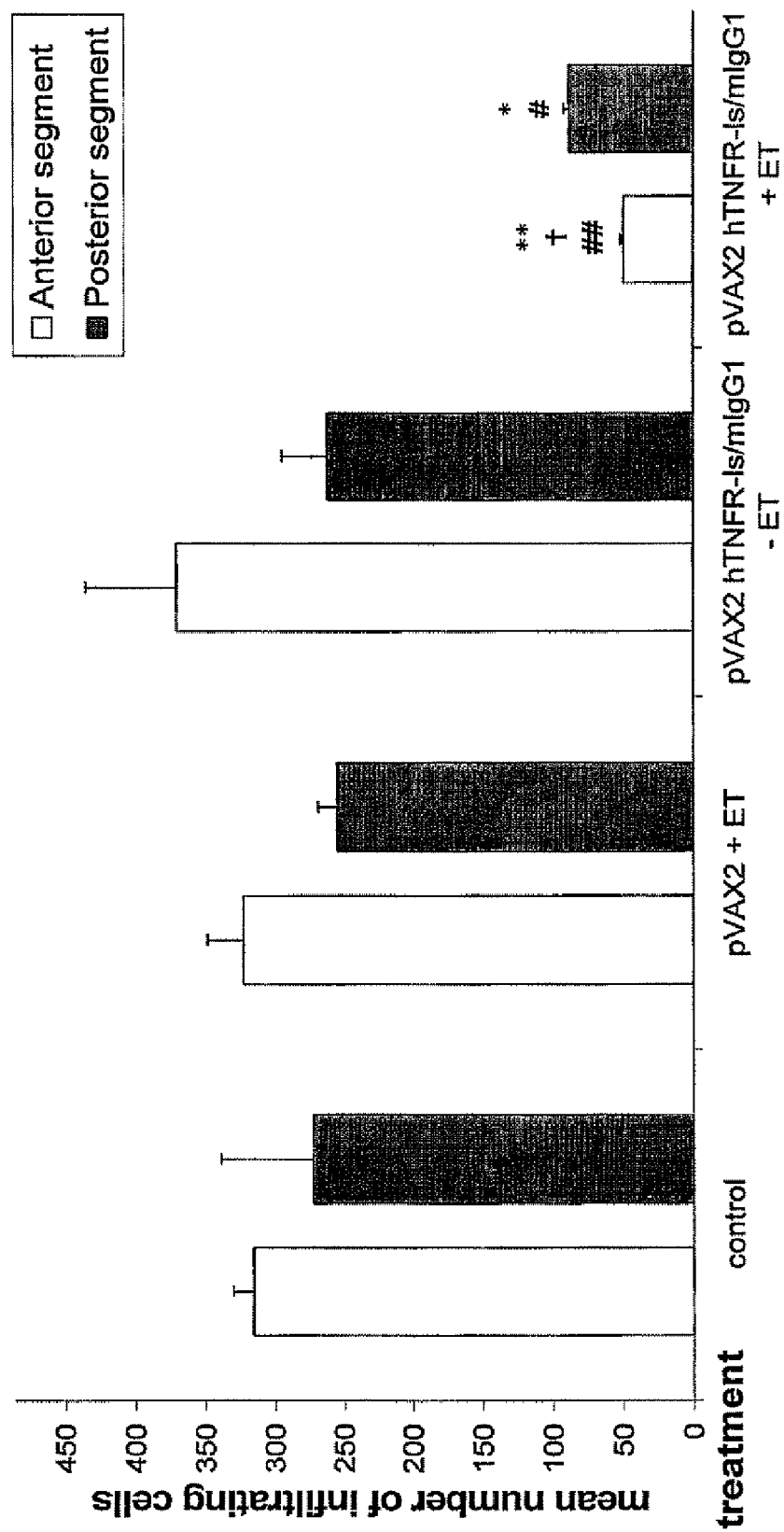
Figure 8B:
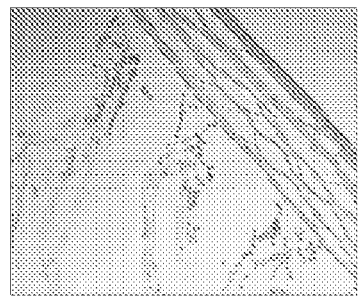
Figure 8E:
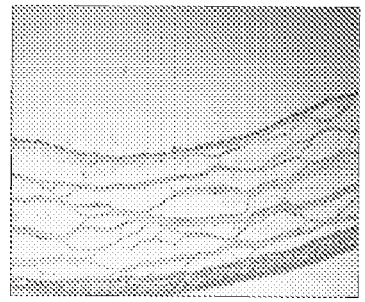
Figure 8C:
Figure 8F:
Figure 8D:
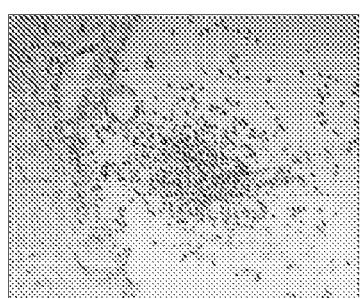
Figure 8G:
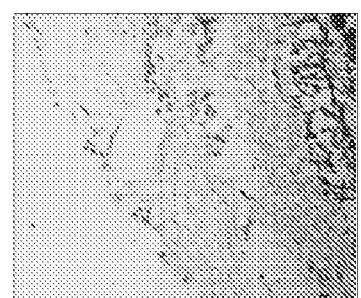

In the rats treated with 3 μg of pVAX2 hTNFR-Is/mIgG1 intra ciliary muscle injection combined with electrotransfer, a marked reduction of infiltrating cells numbers was observed both in the anterior segment (49±1, P<0.002 versus control and NaCl) and in the posterior segment (88±3, P<0.05 versus control) of these rat eyes (FIGS. 8A and B).

TNF-α Levels in the Aqueous Humor

The mean level of TNF-α in the aqueous humor of Lewis rats with EIU (510±44 pg/ml) was not significantly different than in the group of rats that received saline and electrotransfer (374±65 pg/ml, P=0.10).

The mean level of TNF-α was significantly reduced in the group of rats treated with electrotransfer of 3 μg of pVAX2 hTNFR-Is/mIgG1 (126±16 pg/ml) when compared to rats that received electrotransfer of saline (P<0.002) or to EIU control rats (P<0.0005). In the group of rats that received the injection of 3 μg pVAX2 hTNFR-Is/mIgG1 in the ciliary muscle without electric field delivery, the mean level of TNF-α was 250±45 pg/ml, i.e. not significantly different from the TNF-α level in EIU rats with electrotransfer of saline (P=0.07).

Electrotransfer of the empty plasmid has no effect on TNF-α levels in the aqueous humor when compared to the control saline treated group (478±33 pg/ml, P=0.14).

No TNF-α was detectable in naïve rats.

Discussion

Electrotransfer of plasmid DNA to skeletal muscle is a safe and efficient gene transfer technique which can yield to the expression of high levels of circulating proteins (1; 6-11). Selective electric parameters have been introduced (10, 12, 13, 14).

In the eye, the ciliary muscle is a particular smooth muscle. Some fibres of said muscle are oriented circularly while others are oriented longitudinally or radialy for attachment to the scleral spur. Due to its superficial location, below the sclera, at the crossroad between the anterior and posterior segments, the ciliary muscle has been considered by the inventors as an ideal candidate for the electrotransfer of genes encoding potentially therapeutic proteins. The possible transfection of these genes within the ciliary muscle and the secretion of the encoded proteins in the aqueous humor or in the vitreous is most appealing and was the initial aim of their investigations. To date, no previous attempts to use the ciliary muscle as a target for gene electro-transfer have been made.

To control the intra ciliary muscle injection of plasmid in rat eyes, a tunnel path was created. The tunnel was initiated in the cornea extending towards the limbal area and further backward under the sclera into the ciliary muscle. The active electrode, covered with an isolating material on its whole length except the part inserted into the muscle, was then introduced in the created tunnel. Electrotransfer was performed in a controlled manner reducing risk for electric burn. Using this technique, electrotransfer after intra ciliary injection of saline did not influence the clinical score of EIU and did not increase the levels of TNF-α in the aqueous humor, suggesting that electrotransfer, under these specific conditions, does not induce intraocular inflammation. When intraocular inflammation was already present, as in rats with induced EIU, the reaction was not enhanced and disease process aggravated after electrotransfer.

Inventor's experiments show also that plasmid DNA can be introduced into the ciliary muscle of rat eyes and, efficiently and specifically transfect the muscle cell fibres by application of electrotransfer. Using newly devised electrodes probes for this purpose, inventors have shown that GFP reporter transgenic protein can be specifically localized within the ciliary muscle. Also, they have demonstrated the expression of luciferase activity within the treated eyes for at least 30 days after electrotransfer. Furthermore, after ciliary muscle injection of a plasmid with a gene encoding for human TNF-α soluble receptor and application of electrotransfer, high levels of the soluble receptor protein were measured in the aqueous humor of the treated rats. Interestingly, these rats had no detectable human TNF-α receptor in their serum or in the fellow eye. These findings demonstrate that a local production of proteins with potential therapeutic applications can be achieved and that the locally produced protein remains mostly confined to the treated eye.

Success and reproducibility of electro-transfer depends on an efficient administration of a sufficient amount of plasmid DNA in the target tissue, on a well chosen electric field intensity and on a controlled distance between the two electrodes, since this distance determines the electric field value (in V/cm)(11, 12).

The GFP expression experiments showed that when no electric pulse delivery was applied after injection of a high dose of plasmid (30 µg), cells expressing GFP were sparsely located in the ciliary region. On the other hand, when electrotransfer followed plasmid DNA injection, a high GFP expression was detected in muscle cell fibres, allowing for a sustained production of proteins, as shown by luciferase activity up to one month after electrotransfer.

The extraocular skeletal muscle might be used for similar therapeutic purpose than the ciliary muscle. Indeed, the inventors have discovered a high capacity plasmid electrotransfer into the extraocular muscle.

The beneficial effect of hTNFR-Is/mIgG1 plasmid electrotransfer on EIU resulted from the production of hTNFR-Is in the ocular media, since no effect was observed with the plasmid injected alone or with control electrotransfer (saline and empty plasmid) that did not yield to any therapeutic protein production. This was corroborated by the fact that TNF-α level in the aqueous humor of rats treated with the low plasmid dose (3 µg) combined with electrotransfer was significantly reduced when compared to the levels of TNF-α in the control groups or in the group of rats treated by the simple plasmid injection. In the group of rats treated with electrotransfer of the therapeutic plasmid, the number of infiltrating inflammatory cells was significantly reduced both in the anterior and in the posterior segment of the eye, suggesting that TNFR-Is may have been also produced in the vitreous of treated animals, which is of interest for the treatment of retinal diseases.

TNF-α is a major pro-inflammatory cytokine involved in the pathogenesis of intraocular inflammation (15, 16). Its exact mechanism of action remains incompletely understood (17). But, evident beneficial effects on ongoing intraocular inflammatory disease processes are obtained by the use of TNF-α blocking agents during experimental (18, 19) and clinical ocular inflammatory diseases (20, 21, 22). TNF-α binds to membrane bound receptors TNFR-I (p55,55 kd) or TNFR-II (p75, 75 kd). The naturally occurring soluble forms of these two receptors neutralize the pro-inflammatory activity of TNF-α but are highly unstable. Therefore, in the clinic, anti TNF strategies use either monoclonal antibodies against TNF (Infliximab and Adalimumab) or TNF-α soluble receptors stabilized by an immunoglobulin fragment, TNFR-IIs/Fc (Etanercept) or TNFR-Is/Fc (Lenercept). Systemic treatment with Etanercept reduces the clinical scores of EIU and ocular cell infiltration (19). Patients with posterior intraocular inflammation treated with TNFR-Is/Ig (p55) administered systemically had an evident clinical improvement along with the finding of an increase in the number of peripheral blood $CD4^+T$ cells expressing IL-10 (23). However, systemic administration of anti TNF-α is associated with severe side effects (22). Inventor's experiments show that the local intraocular production of TNFR-Is by ciliary muscle fibres after electrotransfer of hTNFR-Is/mIgG1 plasmid, reduces significantly the intensity of clinical and histological disease parameters in EIU. In these treated EIU rats, no detectable levels of TNFR-Is were found in the serum. Thus, ciliary muscle electrotransfer of hTNFR-Is/mIgG1 plasmid can be an alternative to systemic administration of anti-TNF-α in patients suffering of severe intraocular inflammation refractory to other medical therapy.

In conclusion, this is the first demonstration that the ocular ciliary muscle or extraocular muscle of the rat eye can be targeted for plasmid electrotransfer, yielding efficient transfection rate, high levels and long standing expression of encoded proteins in the aqueous humor. As a proof of concept, this technique was successfully applied for the treatment of rats with EIU. Electro-transfer of hTNFR-Is/mIgG1 encoding plasmid significantly reduced ocular disease intensity assessed clinically and by histology. This type of therapy opens new and interesting avenues for the treatment of ocular diseases.

REFERENCES AND NOTES

1. Bloquel, C., Fabre, E., Bureau, M. F. & Scherman, D. Plasmid DNA electrotransfer for intracellular and secreted proteins expression: new methodological developments and applications. *J Gene Med.* 6 Suppl 1, S11-23 (2004).
2. Hoekzema, R., Verhagen, C., van Haren, M. & Kijlstra, A. Endotoxin-induced uveitis in the rat. The significance of intraocular interleukin-6. *Invest Ophthalmol Vis Sci.* 33, 532-539 (1992).
3. Rosenbaum, J. T., McDevitt, H. O., Guss, R. B. & Egbert, P. R. Endotoxin-induced uveitis in rats as a model for human disease. *Nature.* 286, 611-613 (1980).
4. de Vos, A. F., Klaren, V. N. & Kijlstra, A. Expression of multiple cytokines and IL-1RA in the uvea and retina during endotoxin-induced uveitis in the rat. *Invest Ophthalmol Vis Sci.* 35, 3873-3883 (1994).
5. Behar-Cohen, F. F. et al. Iontophoresis of dexamethasone in the treatment of endotoxin-induced-uveitis in rats. *Exp Eye Res.* 65, 533-545 (1997).
6. Bettan, M. et al. High-level protein secretion into blood circulation after electric pulse-mediated gene transfer into skeletal muscle. *Mol Ther.* 2, 204-210 (2000).
7. Aihara, H. & Miyazaki, J. Gene transfer into muscle by electroporation in vivo. *Nat Biotechnol,* 16, 867-870 (1998).
8. Cappelletti, M. et al. Gene electro-transfer improves transduction by modifying the fate of intramuscular DNA. *The Journal of Gene Medicine.* 5, 324-332 (2003).
9. Komamura, K. et al. Treatment of dilated cardiomyopathy with electroporation of hepatocyte growth factor gene into skeletal muscle. *Hypertension.* 44, 365-371 (2004).
10. Rubenstrunk, A., Mahfoudi, A. & Scherman, D. Delivery of electric pulses for DNA electrotransfer to mouse muscle does not induce the expression of stress related genes. *Cell Biol Toxicol.* 20, 25-31 (2004).
11. Bureau, M. F. et al. Intramuscular plasmid DNA electrotransfer: biodistribution and degradation. *Biochim Biophys Acta.* 1676, 138-148 (2004).
12. Molnar, M. J. et al. Factors influencing the efficacy, longevity, and safety of electroporation-assisted plasmid-based gene transfer into mouse muscles. *Mol Ther.* 10, 447-455 (2004).
13. Dean, D. A. Electroporation of the vasculature and the lung. *DNA Cell Biol.* 22, 797-806 (2003).
14. Satkauskas S., et al al. Mechanisms of in vivo DNA electrotransfer: respective contributions of cell electropermeabilization and DNA electrophoresis. *Molecular Therapy,* 2002, Vol. 5 n°2, 133-140.

15. Koizumi, K. et al. Contribution of TNF-alpha to leukocyte adhesion, vascular leakage, and apoptotic cell death in endotoxin-induced uveitis in vivo. *Invest Ophthalmol Vis Sci.* 44, 2184-2191 (2003).
16. Santos Lacomba, M. et al. Aqueous humor and serum tumor necrosis factor-alpha in clinical uveitis. *Ophthalmic Res.* 33, 251-255 (2001).
17. De Vos, A. F., Van Haren, M. A., Verhagen, C., Hoekzema, R. & Kijlstra, A. Systemic anti-tumor necrosis factor antibody treatment exacerbates endotoxin-induced uveitis in the rat. *Exp Eye Res.* 61, 667-675 (1995).
18. Dick, A. D., Forrester, J. V., Liversidge, J. & Cope, A. P. The role of tumour necrosis factor (TNF-alpha) in experimental autoimmune uveoretinitis (EAU). *Prog Retin Eye Res.* 23, 617-637 (2004).
19. Avunduk, M. C. et al. Etanercept treatment in the endotoxin-induced uveitis of rats. *Exp Eye Res.* 79, 357-365 (2004).
20. Rosenbaum, J. T. & Smith, J. R. Anti-TNF therapy for eye involvement in spondyloarthropathy. *Clin Exp Rheumatol.* 20, S143-145 (2002).
21. El-Shabrawi, Y. & Hermann, J. Anti-tumor necrosis factor-alpha therapy with infliximab as an alternative to corticosteroids in the treatment of human leukocyte antigen B27-associated acute anterior uveitis. *Ophthalmology.* 109, 2342-2346 (2002).
22. Murphy, C. C. et al. Tumor necrosis factor alpha blockade with infliximab for refractory uveitis and scleritis. *Ophthalmology.* 111, 352-356 (2004).
23. Greiner, K. et al. Anti-TNFalpha therapy modulates the phenotype of peripheral blood CD4+ T cells in patients with posterior segment intraocular inflammation. *Invest Ophthalmol Vis Sci.* 45, 170-176 (2004).

The invention claimed is:

1. A method of treating an ocular disease affecting a subject, comprising administering a therapeutic desoxyribonucleic acid (DNA) encoding a therapeutic substance to the ciliary muscle tissue or cells of the subject to be treated, wherein the administering comprises injecting the therapeutic DNA into the tissue or cells and applying an electric field via electroporation.

2. The method according to claim 1, wherein the therapeutic desoxyribonucleic acid is administered by transscleral, transcorneal, intraocular or endoscopic route.

3. The method according to claim 1, wherein the intensity of the field is between about 1 and 400 volts/cm.

4. The method according to claim 3, wherein the total duration of application of the electric field is between 0.01 and 500 milliseconds.

5. The method according to claim 3, wherein the application of the electric field comprises between 1 and 100 000 pulses of frequency between 0.1 and 1000 hertz.

6. The method according to claim 3, wherein the electric field comprises electrical pulses which are unipolar or bipolar wave pulses.

7. The method according to claim 3, wherein the electric field comprises electrical pulses which are exponentially decreasing waves, oscillating unipolar waves of limited duration or other wave forms.

8. The method according to claim 3, wherein the electric field comprises electrical pulses which are square wave pulses.

9. The method according to claim 6, wherein the electrical pulses comprise oscillating bipolar wave pulses.

10. The method according to claim 1, wherein the administering comprises applying an electric field comprising 8 unipolar square wave pulses, of frequency of 5 Hz, the intensity of each pulse being of 200 volts/cm for a total duration of application of the electric field of 20 ms per pulse.

11. The method according to claim 1, wherein the administering comprises applying an electric field using at least two electrodes distant from each other by less than one centimeter, at least one of said electrodes being introduced into the ciliary muscle tissue or cells.

12. The method according to claim 11, wherein the electrodes are distant from each other by less than 10 millimeters.

13. The method according to claim 11, wherein one electrode is reversibly applied on the surface of the sclera or eye conjunctiva.

14. The method according to claim 13, wherein the electrode is reversibly applied on the surface of the limbic conjunctiva.

15. The method according to claim 3, further comprising performing iontophoresis before, during or after electroporation.

16. The method according to claim 1, wherein the therapeutic desoxyribonucleic acid is a double stranded DNA, a single stranded DNA or a complex DNA, and wherein the therapeutic desoxyribonucleic acid is a plasmid.

17. The method according to claim 1, wherein the therapeutic desoxyribonucleic acid comprises sequences allowing and/or promoting expression in the ciliary muscle tissue or cells.

18. The method according to claim 1, wherein the therapeutic desoxyribonucleic acid is injected in multiple sites.

19. The method according to claim 1, wherein the desoxyribonucleic acid encodes a protein chosen from enzymes, blood derivatives, hormones, lymphokines, cytokines, chimiokines, anti-inflammatory factors, growth factors, trophic factors, neurotrophic factors, haematopoietic factors, angiogenic factors, anti-angiogenic factors, inhibitors of metalloproteinase, regulators of apoptosis, coagulation factors, receptors thereof, a peptide which is an agonist or antagonist of a receptor or of an adhesion protein, antigens, antibodies, fragments thereof or other essential constituents of the cell.

20. The method according to claim 1, wherein the ocular disease is an ocular inflammatory disease, ischemic disease, proliferative disease, neurodegenerative disease or glaucoma.

21. The method according to claim 20, wherein the proliferative disease is a neovascular or glial disease.

22. The method according to claim 1, wherein the ocular disease is scleritis, conjunctivitis, keratitis, endothelitis, uveitis, choroiditis, retinitis, retinochoroiditis, anterior uveitis, retinopathy of prematurity, diabetic retinopathy, proliferative vitreo retinopathy, inherited retinal dystrophies, age-related macular degeneration, open angle glaucoma, neovascular glaucoma or ischemic retinopathy.

* * * * *